U S010232153B2

(12) United States Patent
Nishida et al.

(10) Patent No.: US 10,232,153 B2
(45) Date of Patent: Mar. 19, 2019

(54) THERAPEUTIC INSTRUMENT

(71) Applicants: OSAKA UNIVERSITY, Osaka (JP); HOYA CORPORATION, Tokyo (JP)

(72) Inventors: Kohji Nishida, Toyonaka (JP); Takeshi Soma, Toyonaka (JP); Yusuke Goto, Tokyo (JP); Kikuo Mitomo, Honjo (JP)

(73) Assignees: Osaka University, Osaka (JP); Hoya Corporation, Tokyo (JP)

( * ) Notice: Subject to any disclaimer, the term of this patent is extended or adjusted under 35 U.S.C. 154(b) by 53 days.

(21) Appl. No.: 15/126,553

(22) PCT Filed: Feb. 26, 2015

(86) PCT No.: PCT/JP2015/055624
§ 371 (c)(1),
(2) Date: Oct. 3, 2016

(87) PCT Pub. No.: WO2015/141432
PCT Pub. Date: Sep. 24, 2015

(65) Prior Publication Data
US 2017/0079838 A1    Mar. 23, 2017

(30) Foreign Application Priority Data
Mar. 17, 2014    (JP) ................. 2014-053328

(51) Int. Cl.
*A61M 31/00*    (2006.01)
*A61F 2/00*    (2006.01)
(Continued)

(52) U.S. Cl.
CPC .......... *A61M 31/00* (2013.01); *A61F 2/0095* (2013.01); *A61F 2/148* (2013.01); *A61F 9/007* (2013.01);
(Continued)

(58) Field of Classification Search
CPC ...... A61F 9/0017; A61F 9/0008; A61F 9/007; A61F 2/0095; A61F 2/02; A61F 2/14;
(Continued)

(56) References Cited

U.S. PATENT DOCUMENTS 4,588,395 A    5/1986    Lemelson
4,836,201 A    6/1989    Patton et al.
(Continued)

FOREIGN PATENT DOCUMENTS

EP    2682076 A1    1/2014
JP    2004-024852    1/2004
(Continued)

OTHER PUBLICATIONS

EPO Extended European Search Report dated Nov. 6, 2017 for EPO App. Ser. No. 15764589.6.
(Continued)

*Primary Examiner* — Shefali D Patel
(74) *Attorney, Agent, or Firm* — Henricks Slavin LLP

(57) ABSTRACT

A therapeutic instrument (20), includes: a support member (25) having a tongue-shaped supporting portion (50) for supporting a sheet-like therapeutic agent; a nozzle member (23) having a cylindrical portion (30) in which the supporting portion (50) supporting the therapeutic agent can be housed, and having an opening (34) through which the supporting portion (50) can be loaded and unloaded in/from a tip of the cylindrical portion (30); a syringe unit (22) that acts a positive pressure in the cylindrical portion (30) for pushing-out the therapeutic agent housed in the cylindrical portion (30) together with the supporting portion (50) to outside the cylindrical portion (30) through the opening (34); and a water flow forming part including a plurality of protrusions (53) formed on a surface of the supporting portion (50) so as to form a water flow at a place where the
(Continued)

supporting portion (50) and the therapeutic agent are facing each other, when a medical water is fed into the cylindrical portion (30) in a state in which the therapeutic agent is housed in the cylindrical portion (30) together with the supporting portion (50).

8 Claims, 21 Drawing Sheets

(51) Int. Cl.
*A61F 2/14* (2006.01)
*A61F 9/007* (2006.01)
*A61F 9/00* (2006.01)

(52) U.S. Cl.
CPC .......... *A61F 9/0008* (2013.01); *A61F 9/0017* (2013.01); *A61F 9/00736* (2013.01); *A61M 2205/04* (2013.01); *A61M 2210/0612* (2013.01)

(58) Field of Classification Search
CPC ........ A61F 2/142; A61F 2/148; A61F 9/0026; A61F 9/00736; A61M 31/00; A61M 2205/04; A61M 2210/0612
USPC ....................................................... 604/272
See application file for complete search history.

(56) References Cited

U.S. PATENT DOCUMENTS

| | | | |
|---|---|---|---|
| 4,880,000 A | 11/1989 | Holmes et al. | |
| 6,554,803 B1 | 4/2003 | Ashman | |
| 7,048,710 B1 | 5/2006 | Cragg et al. | |
| 9,539,139 B2 * | 1/2017 | Andino | A61F 9/0017 |
| 9,808,372 B2 | 11/2017 | Inoue et al. | |
| 2005/0214259 A1 | 9/2005 | Sano et al. | |
| 2006/0259008 A1 | 11/2006 | Orilla | |
| 2007/0208422 A1 | 9/2007 | Walter et al. | |
| 2008/0281341 A1 | 11/2008 | Miller et al. | |
| 2008/0294093 A1 | 11/2008 | Maeda et al. | |
| 2013/0245554 A1 | 9/2013 | Inoue et al. | |
| 2013/0253529 A1 * | 9/2013 | Walter | A61F 2/142 |
| | | | 606/107 |
| 2014/0012278 A1 | 1/2014 | Mita | |

FOREIGN PATENT DOCUMENTS

| | | |
|---|---|---|
| JP | 2008-173333 | 7/2008 |
| JP | 2009-000511 | 1/2009 |
| JP | 2009-524486 | 7/2009 |
| JP | 2014-014398 | 1/2014 |
| WO | WO 2007/089508 A2 | 8/2007 |
| WO | WO 2012/018006 A1 | 2/2012 |

OTHER PUBLICATIONS

International Preliminary Examination Report dated Sep. 29, 2016 for PCT App. Ser. No. PCT/JP2015/055624.

\* cited by examiner

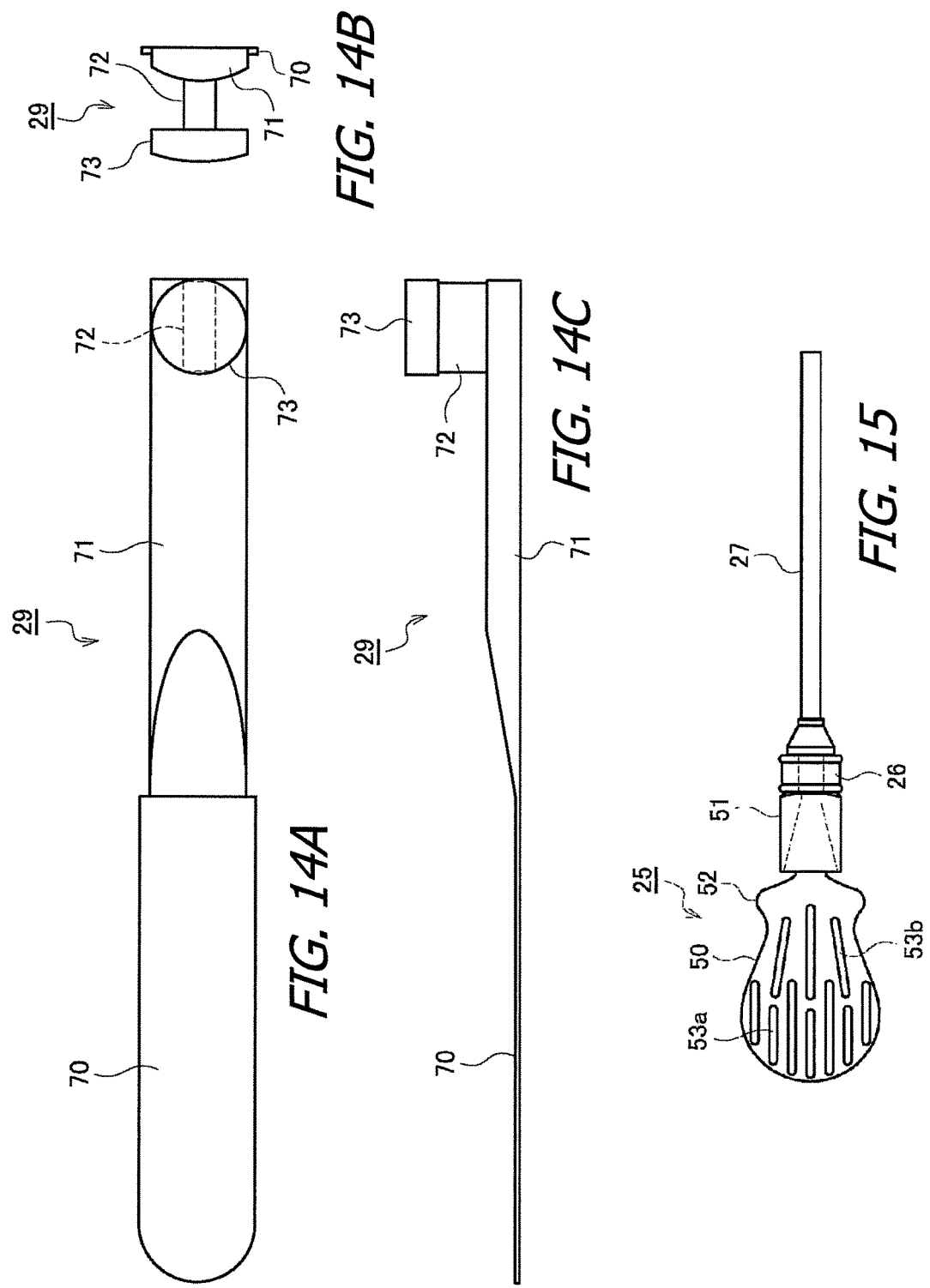

THERAPEUTIC INSTRUMENT

TECHNICAL FIELD

The present invention relates to a suitable therapeutic instrument used for providing a therapeutic agent to an affected area.

DESCRIPTION OF RELATED ART

Currently, there is proposed many treatment techniques for culturing a cell taken from a patient or a donor into a sheet, which is then reproduced, and transplanting the cell sheet to the affected area (for example, see patent document 1). There is a widespread scope of application of the treatment techniques using the cell sheet. For example, such a kind of treatment technique is applied to a treatment of corneal endothelial dysfunction and a treatment of lost tissue of retina in an ophthalmic field, and also to a treatment myocardial infarction and a treatment of endoscopic resection point in a digestive tract wall, etc. Such a kind of treatment requires a low degree of invasion to a human body when the cell sheet is supplied to the affected area, a protection of a fragile cell sheet, a proper shape into which the cell sheet is expanded during transplantation without damaging the cell sheet, and excellent workability during transplantation.

As a therapeutic instrument for feeding a sheet-like therapeutic agent such as the abovementioned cell sheet to the affected area, an applicant of the present invention proposes an instrument including a cylindrical outer tube; a slide member slidably supported in the outer tube; and a sheet-like support member provided at a tip part of the slide member and supporting the sheet-like therapeutic agent, kept in a flat expanded state in a free state of being protruded from a tip of the outer tube, and housed in the outer tube while being deformed into a roll-shape by abutting on the tip part of the outer tube when moving in a direction of an interior of the outer tube in association with a slide movement of the slide member (specifically, see patent document 2).

Further, conventionally, there is also proposed a medical tool specifically for a deep corneal endothelial transplantation (DLEK) (see patent document 3). This medical tool is configured to support a corneal donor disk by a flexible substrate protruded from a tool body, and load and unload the flexible substrate into/from the tool body by a mechanical drive mechanism by a plunger, etc.

The therapeutic instrument described in the patent document 2 has an advantage that it can be obtained at a relatively low cost, and it is easy to be handled. However, the sheet-like support member is expanded together with the therapeutic agent during transplantation into the cornea portion, and therefore such a therapeutic instrument is unsuitable for the transplantation to a narrow space.

In contrast, the medical tool described in the patent document 3 involves the following problem. That is, there is a problem that when the flexible substrate supporting the cornea donor disk, is drawn by the drive mechanism and housed in the tool body, the cornea donor disk is caught by the tool body, resulting in an incomplete storage of the cornea donor disk. As a result, when the cornea donor disk is pushed-out from the tool body, the cornea disk is sometimes clog in the tool body, and therefore there is a lack of reliability in such a medial tool.

Therefore, the applicant of the present invention proposes the therapeutic instrument capable of increasing a reliability of push-out, when the sheet-like therapeutic agent is housed in a cylindrical space, and the therapeutic agent is pushed-out therefrom and fed to the affected area (see patent document 4). Such a therapeutic instrument is the therapeutic instrument for housing the sheet-like therapeutic agent, and feeding the housed therapeutic agent to the affected area, and includes a cylindrical portion that forms a space in which the therapeutic agent can be housed in a deformed state, and also includes a nozzle member having an opening on the tip of the cylindrical portion for loading and unloading the therapeutic agent, and a pressure generator that selectively applies a negative pressure or a positive pressure in the cylindrical portion of the nozzle member. When the therapeutic agent is housed in the cylindrical portion, the space of the cylindrical portion is the space for sucking the therapeutic agent into the cylindrical portion by applying the negative pressure in the cylindrical portion by the pressure generator. Further, when the therapeutic agent housed in the cylindrical portion by sucking is fed to the affected area, the space of the cylindrical portion is the space for pushing-out the therapeutic agent to outside the cylindrical portion by adding the positive pressure in the cylindrical portion by the pressure generator.

PRIOR ART DOCUMENT

Patent Document

Patent document 1: Japanese Patent Laid Open Publication No. 2004-24852
Patent document 2 Japanese Patent Laid Open Publication No. 2009-511
Patent document 3: Japanese Unexamined Patent Application Publication No. 2009-524486
Patent document 4: International Publication No. 2012/018006 Pamphlet

SUMMARY OF THE INVENTION

Problem to be Solved by the Invention

However, as a result of strenuous efforts by the inventors of the present invention regarding the therapeutic instrument described in the abovementioned patent document 4, the following new problem is found. Explanation will be given hereafter.

When the therapeutic instrument described in patent document 4 is used in a normal ophthalmic surgery, the task of housing the therapeutic agent in the cylindrical portion is performed immediately before feeding the therapeutic agent to an eyeball of a patient. Therefore, the time from housing the therapeutic agent in the cylindrical portion to push-out it to outside the cylindrical portion, is considered to be about 2 to 3 minutes at longest. The therapeutic agent can be pushed-out to outside the cylindrical portion without particular problem in such a degree of time.

However, in an ophthalmic surgery, there is a case in which the surgery does not necessarily proceed as originally planned. For example, when the therapeutic instrument is used, there is a case in which an intraocular pressure of the patient is too weak and adjustment is required, when the therapeutic agent is housed in the cylindrical portion ready for use, and trying to provide the therapeutic agent to the affected area. In such a circumstance, the therapeutic agent remains to be housed in the cylindrical portion until end of the adjustment of the intraocular pressure. Therefore, when the therapeutic agent is fed to the affected area after end of the adjustment of the intraocular pressure, a considerable time (for example five minutes) is elapsed after the therapeutic agent is housed in the cylindrical portion.

In such a case, it is confirmed by the inventors of the present invention, that the following inconvenience occurs, because the therapeutic agent is housed in the cylindrical portion for a longer time.

That is, when the sheet-like therapeutic agent is supported by a tongue-shaped supporting portion and the therapeutic agent is housed in the cylindrical portion together with the supporting portion for a longer time, it is found that the therapeutic agent is stuck to the supporting portion and is hardly pushed-out satisfactorily. Once such a situation occurs, the therapeutic agent is reset in another therapeutic instrument for reuse. However, when the reuse is difficult, an expensive medical material is wasted.

Such a problem possibly occurs not only in the therapeutic instrument described in the patent document 4, but also in the therapeutic instrument described in the patent document 2 or the patent document 3.

A main object of the present invention is to provide the therapeutic instrument capable of smoothly pushing-out the therapeutic agent to outside the cylindrical portion, even if the therapeutic agent is housed in the cylindrical portion for a longer time.

Means for Solving the Problem

A first aspect of the present invention is a therapeutic instrument, including:

a support member having a tongue-shaped supporting portion for supporting a sheet-like therapeutic agent;

a nozzle member having a cylindrical portion in which the supporting portion supporting the therapeutic agent can be housed, and having an opening on a tip of the cylindrical portion, through which the supporting portion can be loaded and unloaded in/from the cylindrical portion;

a positive pressure generator that adds a positive pressure in the cylindrical portion for pushing-out the therapeutic agent housed in the cylindrical portion together with the supporting portion, to outside the cylindrical portion through the opening; and a water flow forming part that forms a water flow at a place where the supporting portion and the therapeutic agent are faced each other, when a medical water is fed into the cylindrical portion in a state in which the therapeutic agent is housed in the cylindrical portion together with the supporting portion.

A second aspect of the present invention is the therapeutic instrument of the first aspect, wherein the positive pressure generator is configured to generate a positive pressure in the cylindrical portion by feeding a medical water into the cylindrical portion from a rear end side of the cylindrical portion, and the water flow forming part includes one or a plurality of protrusions formed on a surface of the supporting portion for supporting the therapeutic agent by floating it from the surface of the supporting portion, and configured to form a water flow by introducing the medical water fed by the positive pressure generator to a place where the supporting portion and the therapeutic agent are faced each other.

A third aspect of the present invention is the therapeutic instrument of the second aspect, wherein in the plurality of protrusion, a protruding dimension of a protrusion positioned on an upstream side of the water flow formed by the water flow forming part, is set to be larger than a protruding dimension of a protrusion positioned on a downstream side thereof.

A fourth aspect of the present invention is the therapeutic instrument of any one of the first to third aspects, wherein the water flow forming part includes a first through hole formed on the cylindrical portion, and a second through hole formed on the supporting portion so as to correspond to the first through hole, and overlapped on the first thorough hole in a state in which the supporting portion is housed in the cylindrical portion, and is configured to form a water flow at a place where the supporting portion and the therapeutic agent are faced each other, when a medical water is injected into the cylindrical portion through the first through hole and the second through hole in a state in which the supporting portion supporting the therapeutic agent is housed in the cylindrical portion.

A fifth aspect of the present invention is the therapeutic instrument of any one of the first to fourth aspects, wherein the water flow forming part includes a first notch formed on a tip of the cylindrical portion, and a second notch formed on a tip of the supporting portion so as to correspond to the first notch, and overlapped on the first notch in a state in which the supporting portion is housed in the cylindrical portion, and is configured to form a water flow at a portion where the supporting portion and the therapeutic agent are faced each other, when a medical water is fed into the cylindrical portion from a place where the first notch and the second notch are overlapped on each other in a state in which the supporting portion supporting the therapeutic agent is housed in the cylindrical portion.

Advantage of the Invention

According to the present invention, the therapeutic agent can be smoothly pushed-out to outside the cylindrical portion, even if the therapeutic agent is housed in the cylindrical portion for a longer time.

BRIEF DESCRIPTION OF THE DRAWINGS

FIGS. 14A, 14B and 14C are plan, rear end and lower side views of a pressing membere.

FIG. 15 is a view illustrating an assembly in a state in which the sealing member and the needle member are attached to the support member.

DETAILED DESCRIPTION OF THE INVENTION

Figure 1:
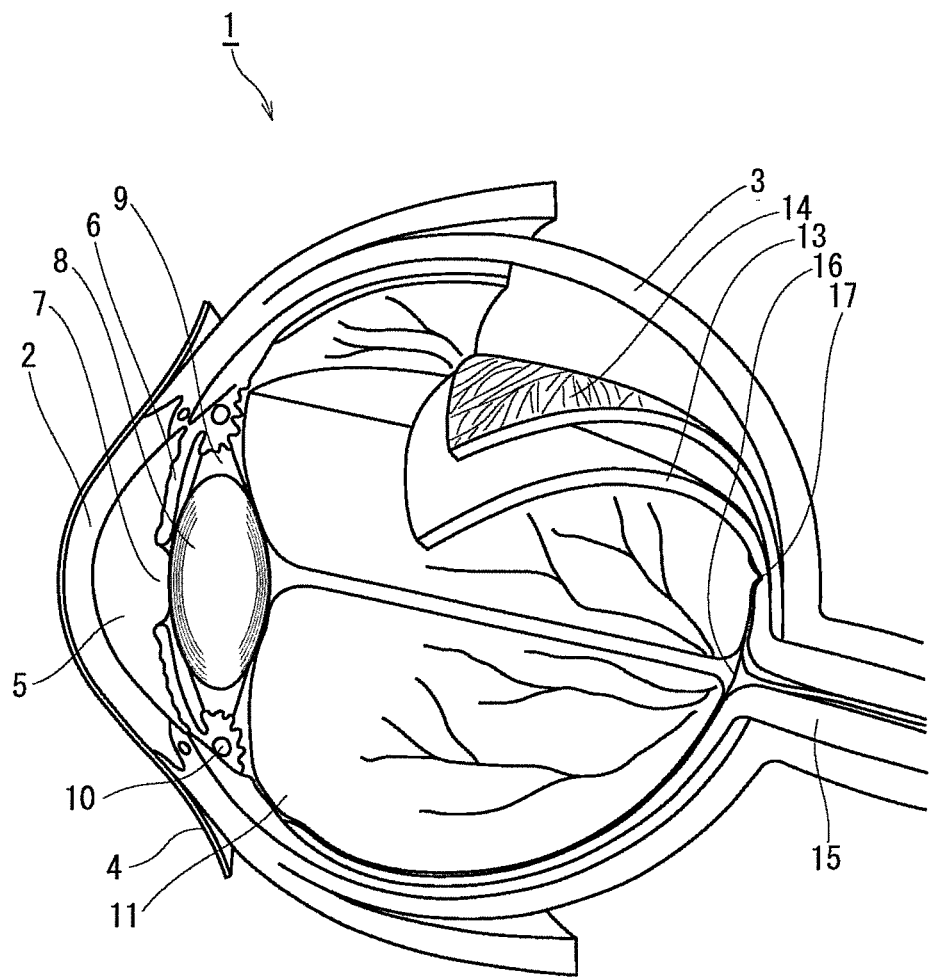
FIG. 1 is a view illustrating a planar cross-sectional structure of an eyeball.

When the therapeutic instrument of the present invention is used as a surgery instrument used in an ophthalmic surgery, more specifically, when used as the therapeutic instrument used in corneal endothelium transplant surgery (DSAEK) effective for a treatment of corneal endothelial cell disorder for example, an embodiment in this case will be described hereafter in detail, with reference to the drawings. The therapeutic instrument of the present invention is not limited to an application to ophthalmic surgery instruments, and can be used as a medical surgery instrument other than an ophthalmic field, and further an instrument of a common use other than a medical use, for example, as each kind of instrument for experiments (or test).

An embodiment of the present invention will be described in the following order.

1. Structure of an eyeball
2. Configuration of a therapeutic instrument of a first embodiment
3. Method of manufacturing the therapeutic instrument (assembly procedure)
4. Method of using the therapeutic instrument
5. Effect of a first embodiment
6. Explanation for a second embodiment
7. Explanation for a third embodiment
8. Explanation for a fourth embodiment
9. Explanation for a fifth embodiment
10. Modified example, etc.

1. Structure of an Eyeball

Overall Structure of an Eyeball

FIG. 1 is a view illustrating a planar cross-sectional structure of an eyeball. As illustrated in the figure, an eyeball 1 has a spherical shape as a whole, and is covered and protected by a sclera 3 except for a frontward cornea 2. A surface of the sclera 3 around the cornea 2 is covered with a conjunctiva 4. The cornea 2 has a lens function of refracting a light coming from outside, in addition to an eyeball protecting function. There is an anterior chamber 5 filled with aqueous humor on the inside (back side) of the cornea 2, and there is a pupil 7 in the center of an iris 6 facing the anterior chamber 5.

The iris 6 has a function of adjusting a light quantity incident on the inside of the eyeball 1, by adjusting a size (dimension of an opening) of the iris 7. A front side of a lens 8 is disposed to face the iris 7. A ciliary body 10 is connected to the lens 8 via a zonules 9. The ciliary body 10 is a muscle tissue that performs focusing by controlling a thickness of the lens 8.

There is a vitreous body 11 on the back side of the lens 8. The vitreous body 11 occupies a large part of an interior of the eyeball 1. The vitreous body 11 is a jelly-like colorless transparent tissue, and maintains a shape and elasticity of the eyeball 1. Further, the vitreous body 11 serves as a body to send a light beam refracted by the lens 8, to a retina 13. The retina 13 is a membrane tissue located at an innermost side in the interior of the eyeball 1. There are visual cells in the retina 13, to feel a light incident on the interior of the eyeball 1 through the pupil 7, and identify intensity, color, and form of the light.

There is a choroid 14 on the outside of the retina 13. The choroid 14 is a membrane tissue located at the inside of the sclera 3 (namely, between the sclera 3 and the retina 13). The choroid 14 is rich in blood vessels, and serves as a membrane to nourish the interior of the eyeball 1, as a blood flow path to each organization of the eyeball 1. Further, an optic nerve 15 is connected to the back side (rear side) of the eyeball 1. The optic nerve 15 is a nerve to transmit a light stimulus received by the retina 13 to a brain. There is a blind spot 16 at a portion to which the optic nerve 15 is connected. The blind spot 16 is located at a portion away from a fovea 17 by 4 to 5 mm.

A Structure of the Cornea

Figure 2:
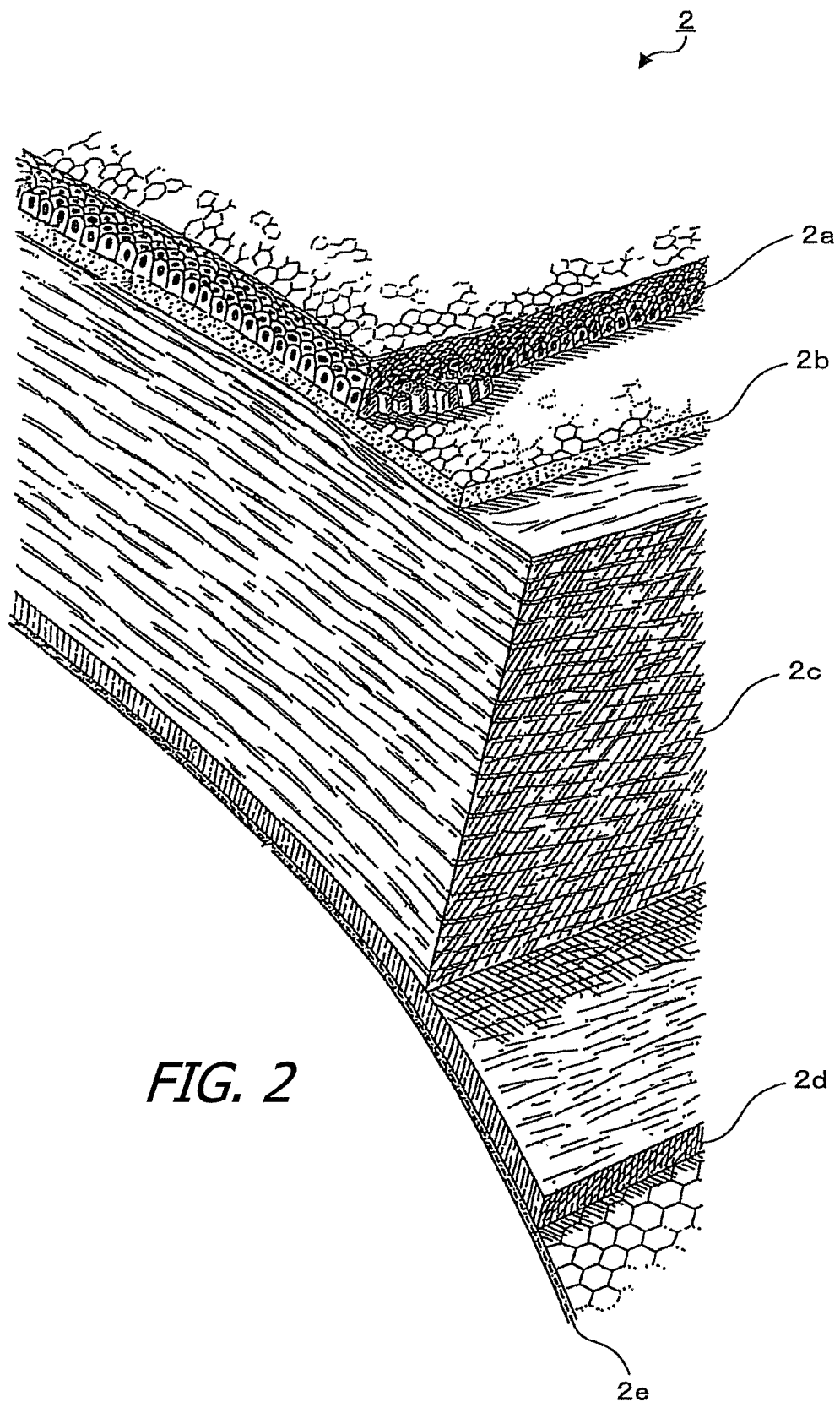
FIG. 2 is a schematic view illustrating a structure of a cornea three-dimensionally.

FIG. 2 is a schematic view illustrating the structure of the cornea three-dimensionally. The cornea 2 has a lamination structure of multiple layers. Specifically, the cornea 2 has a structure of laminating a corneal epithelial layer 2a, a bowman's membrane 2b, a corneal stromal layer 2c, a descemet's membrane (inner limiting plate) 2d, and a corneal endothelium layer 2e.

The corneal epithelial layer 2a exists on an outermost layer of the cornea 2, and composed of five to six layers of stratified squamous epithelial cells. The bowman's film 2b exists between the corneal epithelial layer 2a and a corneal stroma layer 2c, and composed of collagen fibers with a thickness of about 10 µm.

The corneal stromal layer 2c exists between the bowman's film 2b and the descemet's membrane 2d, and occupies 90% of a total corneal layer. The descemet's membrane 2d exists between the corneal stromal layer 2c and the corneal endothelium layer 2e, and composed of fine fibers with a thickness of 5 to 10 µm. The corneal endothelium layer 2e exists on an innermost side of the cornea 2, and composed of a flat hexagonal one layer cell (corneal endothelial cell) with a thickness of 5 µm.

2. Configuration of the Therapeutic Instrument of a First Embodiment

Figure 3:
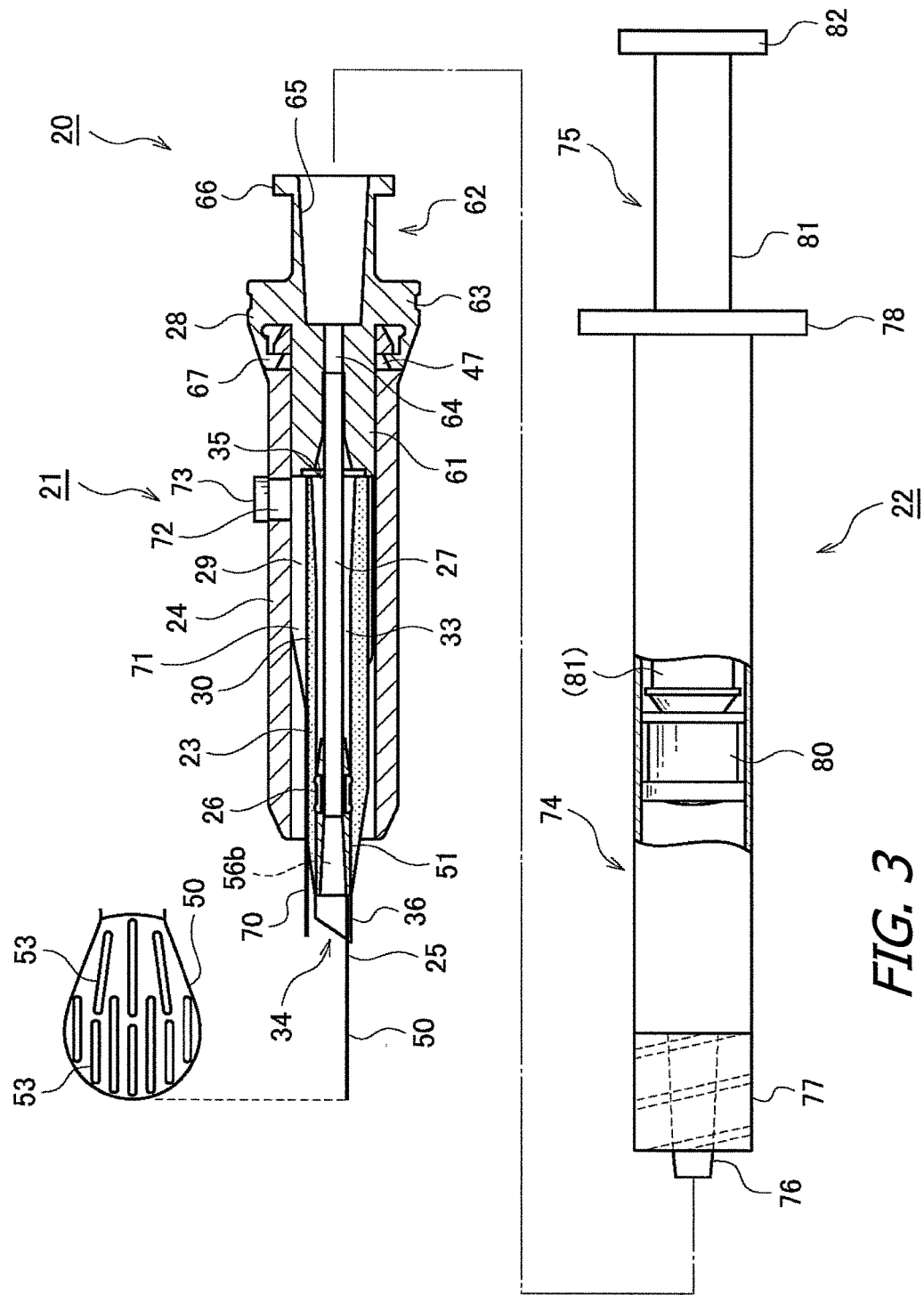
FIG. 3 is a view illustrating a configuration of a therapeutic instrument according to an embodiment of the present invention.

FIG. 3 is a view illustrating a configuration of the therapeutic instrument according to an embodiment of the present invention. A therapeutic instrument 20 illustrated in the figure is the instrument for storing a sheet-like therapeutic agent and feeding the stored therapeutic agent to an affected area.

In this embodiment, as described above, it is assumed to use the therapeutic instrument for a surgery of a corneal endothelium transplantation effective for a treatment of a corneal endothelial cell disorder. Therefore, the therapeutic instrument of this embodiment is one of the instruments for surgery handled by ophthalmologist who performs a corneal endothelium transplantation surgery. Further, in such a transplant surgery, for example the corneal endothelium layer cultured from a donor corresponds to the sheet-like therapeutic agent. The corneal endothelial layer used for transplantation is a circular sheet-like material with a diameter of about 8.0 to 9.0 mm. Further, supply of the corneal endothelial layer is performed to a cornea portion (specifically, a corneal transplantation target site of the endothelial layer) of the eyeball, which is a diseased portion.

The therapeutic instrument 20 has a configuration roughly including a body unit 21 and a syringe unit 22. The body unit 21 and the syringe unit 22 are attachable and detachable to/from each other. In the explanation for the configuration of each part, a view of FIG. 3 viewed from an upper side is used as a planar view, and a view of FIG. 3 viewed from a lower side is used as a lower side view.

Configuration of the Body Unit

The body unit 21 roughly includes a nozzle member 23, a holding member 24, a support member 25, a sealing member 26, a needle member 27, a connecting member 28, and a pressing member 29. The configuration of each configuration member will be described hereafter.

Nozzle Member

Figure 4A:
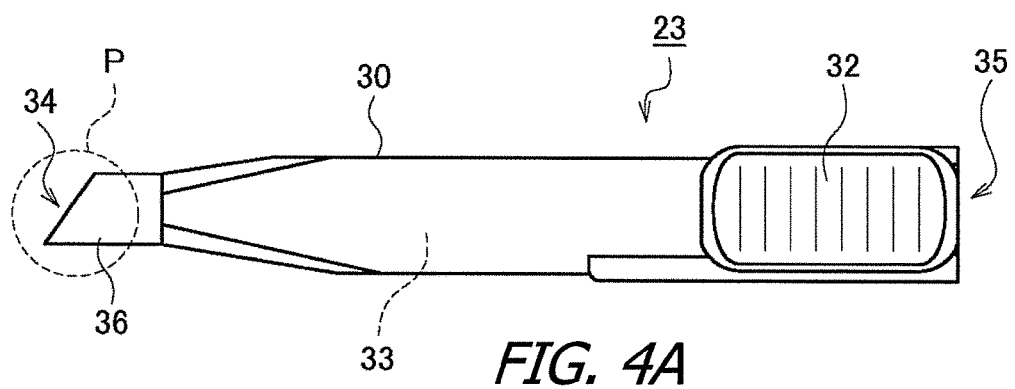
FIGS. 4A and 4B are side and lower side views of a nozzle member.
Figure 4B:
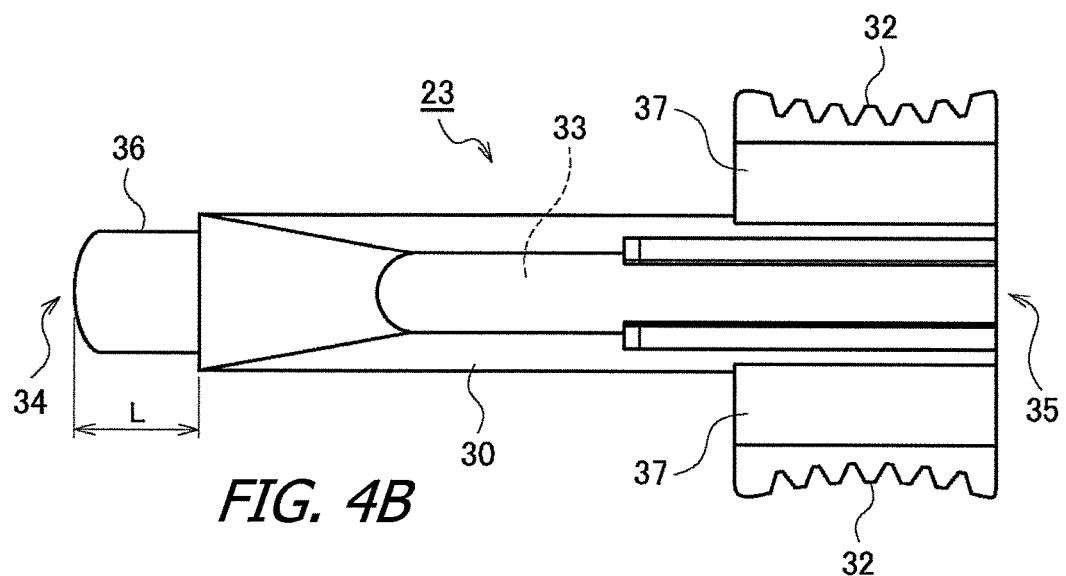
Figure 5A:
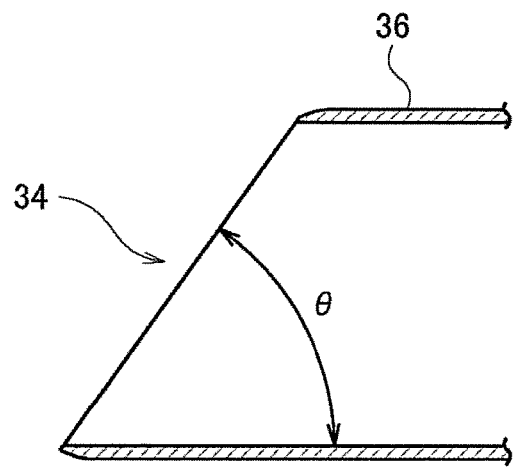
FIG. 5A is an enlarged cross-sectional view of portion P in FIG. 4A
Figure 5B:
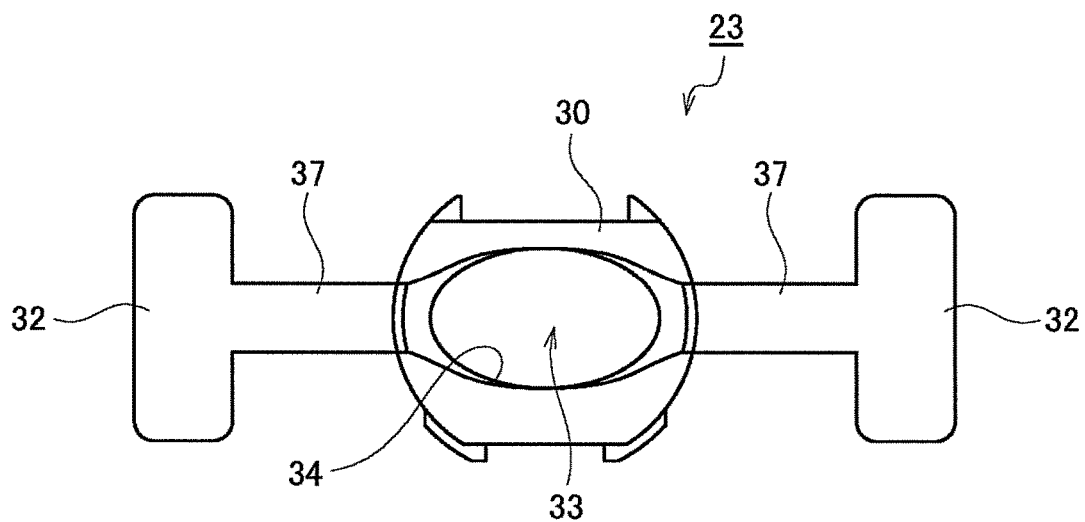
FIG. 5B is an end view of the nozzle member.

FIGS. 4A and 4B illustrate the configuration of the nozzle member, wherein FIG. 4A is a side view and FIG. 4B is a lower side view. Further, FIG. 5A is an expanded cross-sectional view of portion P in FIG. 4A and FIG. 5B is a front end (or "tip end") view of the nozzle member.

The nozzle member 23 has a main function of storing and supplying the corneal endothelial layer serving as a therapeutic agent. The nozzle member 23 is composed of a hollow member obtained by integral molding of resin. When the nozzle member 23 is made of resin, for example polypropylene is suitably used as a material of the nozzle member 23. The nozzle member 23 integrally includes a cylindrical portion 30 and a finger touch portion 32. The cylindrical portion 30 includes a cylindrical space 33 inside. The space 33 is formed into an oval shape in cross-section. Further, the space 33 is formed in a state of penetrating the cylindrical portion 30 in a straight line extending from a tip to a rear end of the cylindrical portion 30 in a central axis direction.

In this specification, when the syringe unit 22 is attached to the body unit 21 to constitute a therapeutic instrument 20 so that the therapeutic agent is fed to the affected area using the therapeutic instrument 20, an end portion disposed at a side closer to the affected area is called a "tip", and an end portion disposed at a side away from the affected area is called a "rear end". Further, when the therapeutic instrument 20 is viewed from a central axis direction, a direction in which a pair of finger touch portion 32 is protruded is called a "horizontal direction", and a direction perpendicular thereto is called a "vertical direction (or height direction)".

The abovementioned space 33 is formed into a uniform cross-sectional shape (oval shape) extending from the tip to the rear end in the axis direction of the cylindrical portion 30, with a uniform opening size. An opening 34 connected to the space 33, is formed at the tip of the cylindrical portion 30, and an opening 35 connected to the space 33, is formed at the rear end of the cylindrical portion 30. Each opening 34, 35 is formed into an oval shape similar to the cross-sectional shape of the space 33. An outer shape of the tip side of the cylindrical portion 30 is narrowed into a taper shape (flat) in a short axis direction of the opening 34. Further, the tip side portion of the cylindrical portion 30 is formed thicker than the narrowed portion, thus forming a beak portion 36 by this thick portion. The beak portion 36 is the portion disposed in a state of facing the affected area, when the therapeutic agent is fed to the affected area. The tip of the beak portion 36 has a shape obliquely cut with respect to the central axis of the nozzle member 23, when the nozzle member 23 is viewed from a side face direction. Then, the opening 34 is formed on this oblique portion. There are mainly two reasons as the reason for forming the tip of the cylindrical portion 30 (beak portion 36) into an oblique cut shape. One of the reasons is that in a pushing process described later, a corneal endothelial layer can be easily inserted into a cornea portion as an example of the affected area. The other reason is that the cylindrical portion 30 (beak portion 36) can be easily inserted into an incision.

The thickness of the beak portion 36 is preferably set to, for example, 0.05 to 0.2 mm, and more preferably set to about 0.1 mm. Further, length L of the beak portion 36 (see FIG. 4B) is preferably set to, for example, in a range of 1 to 7 mm, and more preferably set to about 4 mm. The abovementioned opening 34 is formed in an oblique cut at the tip part of the beak portion 36. An inclination angle θ (see FIG. 5A) of a cut edge of the opening 34 is preferably set to, for example, θ=45 to 60° with respect to the central axis of the cylindrical portion 30, and more preferably set to about 55°, in consideration of facilitating feeding of the therapeutic agent during corneal endothelium transplantation.

A pair of finger touch portion 32 is formed so as to be located at the rear end side of the cylindrical portion 30, namely, at both sides of an outer circumference of the cylindrical portion 30. Each finger touch portion 32 is structurally connected to the cylindrical portion 30 via wing portions 37 corresponding to each finger touch portion 32. Each wing portion 37 is formed into a plate shape in a state of protruding in a diameter direction of the cylindrical portion 30 (long axis direction of the opening 35) from the outer circumference of the cylindrical portion 30. Each wing portion 37 is formed into the plate shape parallel to the long axis, on the long axis of the opening 35.

In contrast, as illustrate in FIG. 5B, a pair of finger touch portion 32 is formed into T-shape as a whole in a combination with the corresponding wing portion 37. Each finger touch portion 32 is formed into the plate shape approximately parallel to the short axis of the opening 35. Concave-shaped dents in planar view are respectively are formed on the outer surface of each finger touch portion 32, in consideration of stability when actually clamping the nozzle member 23, with a fingertip bulb part abutted thereon. Further, in order to suppress the slip of the finger during use of the therapeutic instrument 20, the outer surface of each finger touch portion 32 is formed as an uneven surface in a form in which a plurality of (multiple numbers of) slots are arranged at a prescribed pitch in the axis direction of the cylindrical portion 30.

Holding Member

Figure 6A:
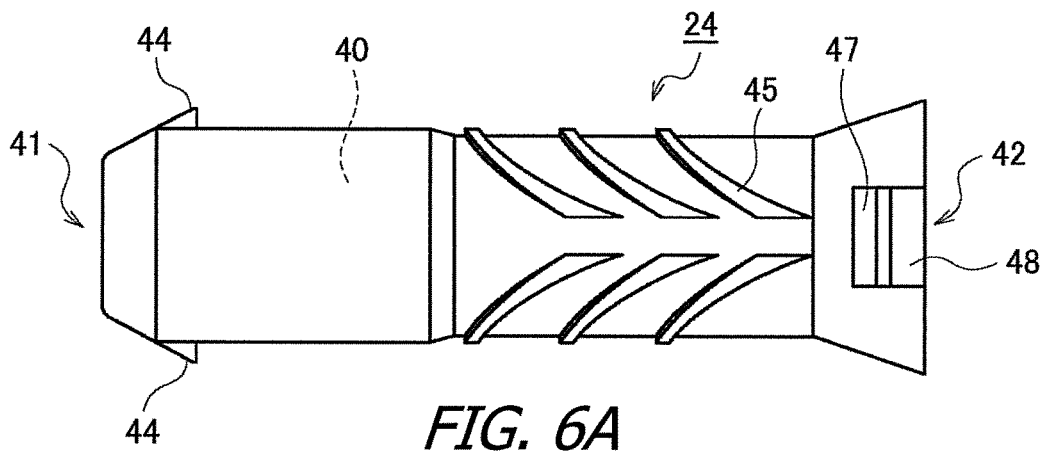
FIGS. 6A, 6B and 6C are lower side, side, and plan views of a holding member.
Figure 6B:
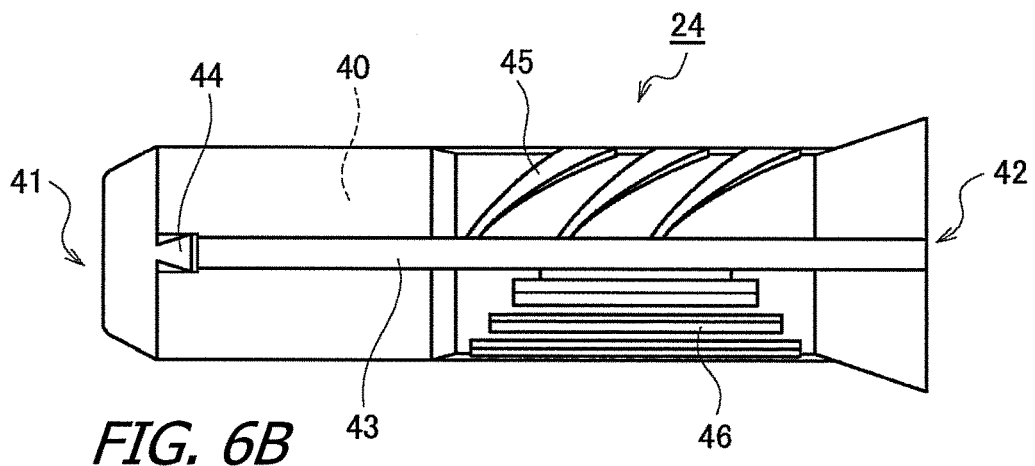
Figure 6C:
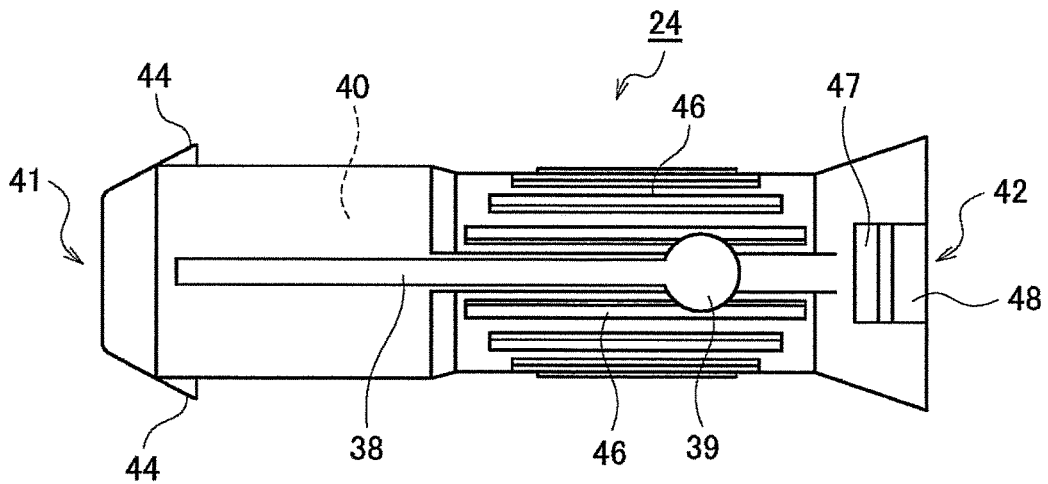
Figure 7A:
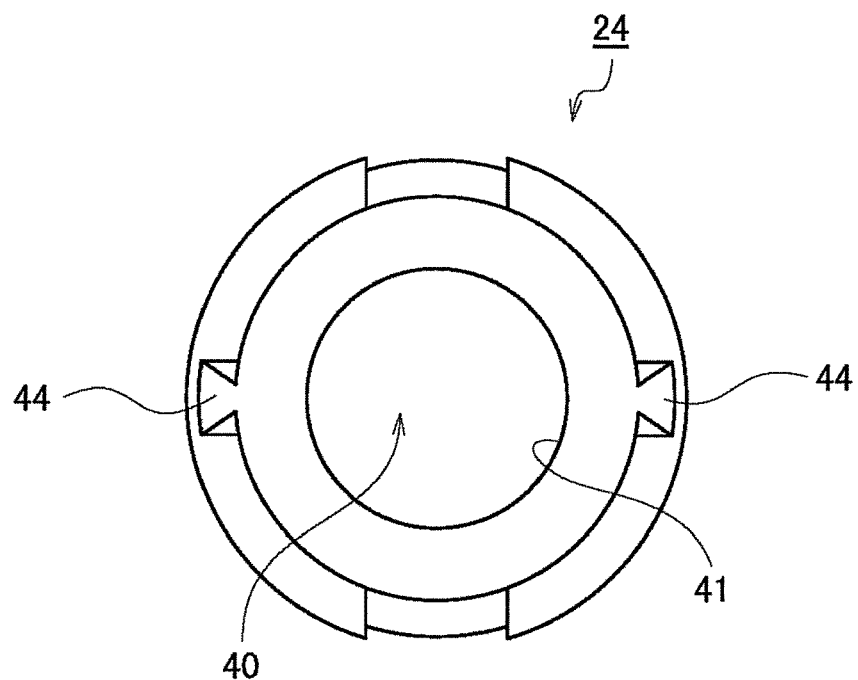
FIGS. 7A and 7B are front end and rear end views of the holding member.
Figure 7B:
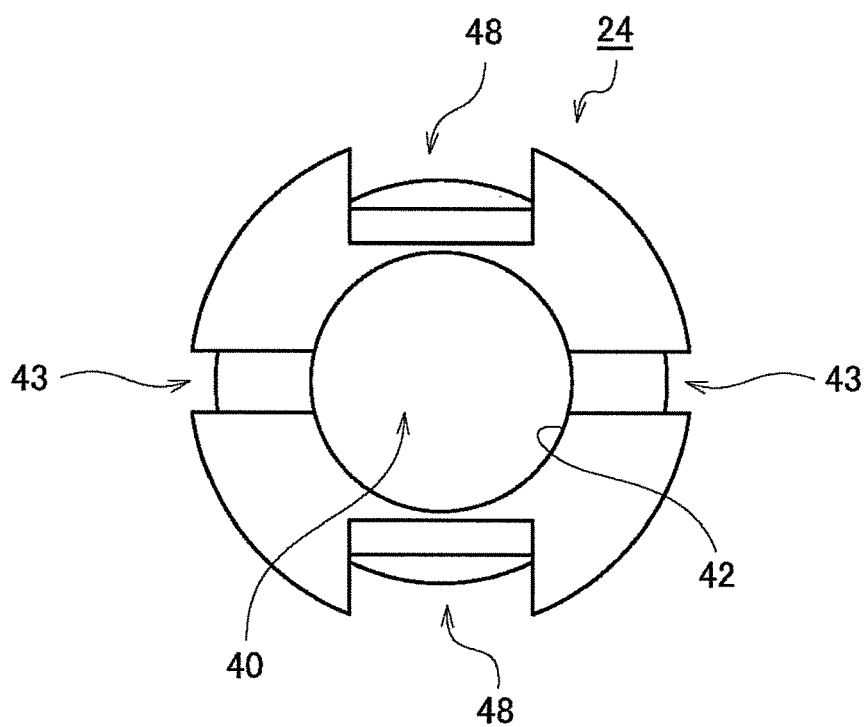

FIGS. 6A, 6B and 6C illustrate a configuration of a holding member, wherein FIG. 6A is a lower side view, FIG. 6B is a side view, and FIG. 6C is a planar view. Further, FIG. 7A is a front end (or "tip end") view of the holding member and FIG. 7B is a rear end view of the holding member.

The holding member 24 is the member for holding the nozzle member 23 so that it can be relatively moved. A "relative movement" described in this specification, is the movement of two structurally independent members relatively to the central axis direction of the body unit 21. The central axis direction of the body unit 21 is the direction that coincides with the central axis direction of the cylindrical portion 30 of the nozzle member 23, the central axis direction of the holding member 24, the central axis direction of the needle member 27, and the central axis direction of the therapeutic instrument 20.

The holding member 24 is the member obtained by an integral molding of resin such as polypropylene for example. The holding member 24 is formed into a cylindrical shape as a whole having a hollow part 40. Circular openings 41 and 42 are respectively formed at the tip and the rear end of the holding member 24. Slits 43 elongated in parallel to the central axis of the holding member 24, are formed as a right and left pair at both sides of the holding member 24. Each slit 43 is formed in a straight line from the opening 42 at the rear end of the holding member 24 to the vicinity of the tip of the holding member 24. A small protrusion 44 is formed at the tip side of the holding member 24. The protrusion 44 is an index for visually recognizing a stop position of the wing portion 37, when the finger is placed on the wing portion 37 to relatively move the nozzle member 23. Namely, when the nozzle member 23 is moved (advanced) to the tip side with respect to the holding member 24, the wing portion 37 approaches the protrusion 44. Then, when the nozzle member 23 is advanced to the vicinity of a termination of the movement, clearance between the protrusion 44 and the wing portion 37 becomes gradually narrower. Therefore, the stop position of the wing portion 37 can be visually recognized by large/small of such a clearance.

Different uneven patterns 45 and 46 are formed on the outer circumference of the holding member 24, in upper and lower parts respectively, with the slit 43 interposed between them. Uneven pattern 45 is the pattern in the form in which approximately V-shaped patterns are arranged in the central axis direction of the holding member 24. Uneven pattern 46 is the pattern in the form in which linear patterns parallel to the central axis of the holding member 24, are arranged in a circumference direction of the holding member 24. Further, a guide groove 38 is formed on the holding member 24. The guide groove 38 is formed into an elongated linear shape in parallel to the central axis direction of the holding member 24. The guide groove 38 is formed in a state of penetrating an outer circumferential wall of the holding member 24. A circular through hole 39 is continuously formed at the rear end portion of the guide groove 38. The guide groove 38 and the through hole 39 are respectively connected to the hollow part 40. A diameter of the through hole 39 is set to be larger than a groove width (short dimension) of the guide groove 38.

The rear end portion of the holding member 24 is formed into a trumpet shape thicker than the other portion. Further, a pair of locking hole 47 is formed on the rear end portion of the holding member 24, in a state of penetrating the holding member 24 in a diameter direction. A pair of locking holes 47 is formed at positions shifted from a pair of slits 43 by 90° phase in the circumferential direction. Further, a pair of notches 48 is formed on the rear end portion of the holding member 24. A pair of notches 48 is formed respectively at a place where the locking holes 47 are formed so as to correspond to the notches 48.

Support Member

Figure 8:
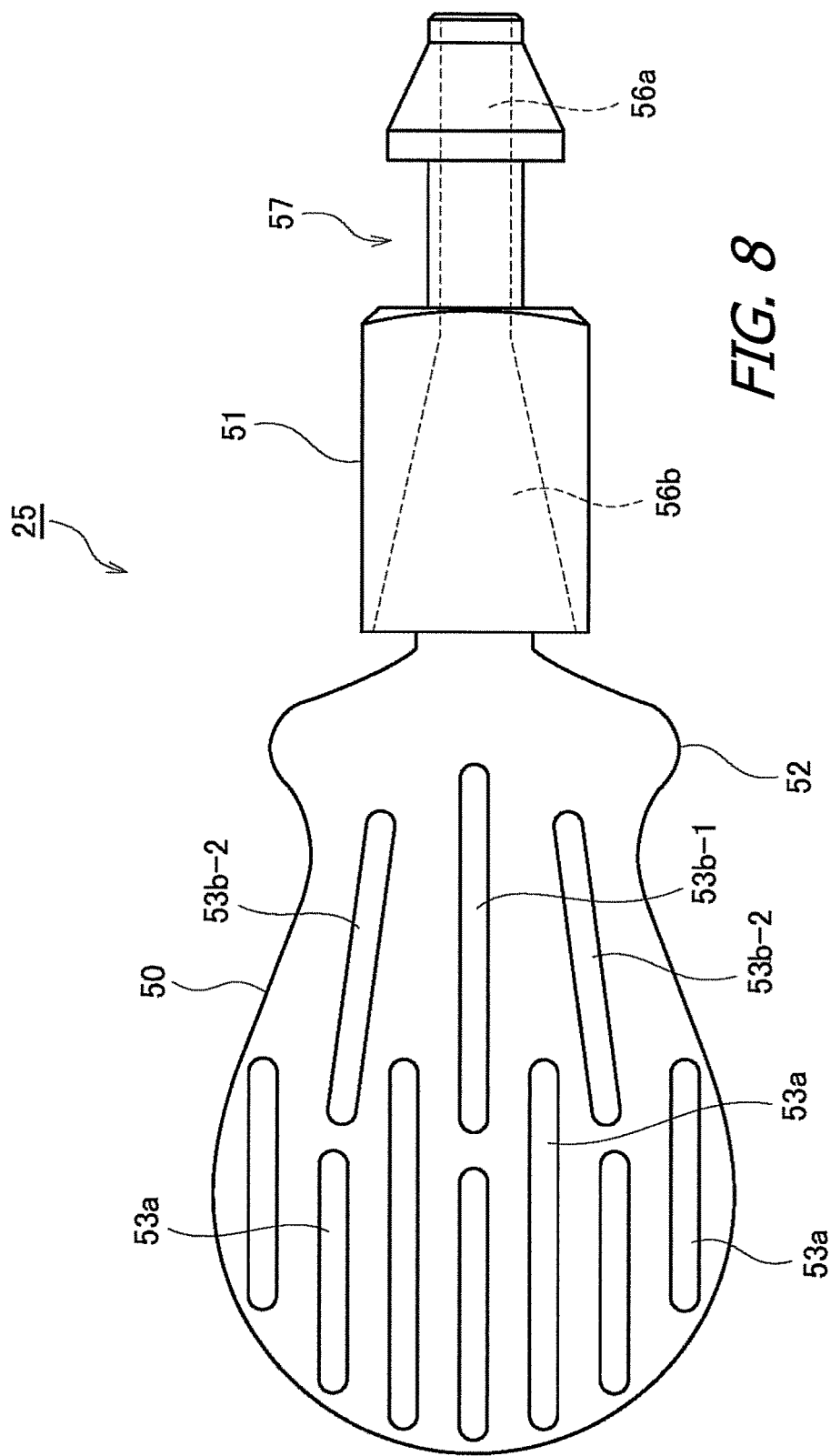
FIG. 8 is a planar view illustrating a configuration of a support member.

FIG. 8 is a planar view illustrating a configuration of a support member.

The support member 25 is the member obtained by an integral molding of resin such as polyethylene for example. The support member 25 integrally has a supporting portion 50 and a base portion 51. The supporting portion 50 is the portion for supporting the corneal endothelial layer as an example of the abovementioned therapeutic agent. The base portion 51 is disposed in the cylindrical portion 30 of the nozzle member 23.

Supporting Portion

The supporting portion 50 is a thin tongue-like (sheet-like) member with a thickness of about 0.08 mm. The supporting portion 50 is substantially a planar expanded state, in a free state with no force added thereon from outside. Further, the supporting portion 50 can be easily deformed when an external force is added thereon. An outer shape (planar shape) of the supporting portion 50 is an "eggplant shape" which is rounded as a whole. The dimension of the outer shape of the rounded portion of the supporting portion 50 may be set to the same dimension as the dimension of the outer shape of the corneal endothelial layer supported by the supporting portion 50, or may be set to a dimension slightly larger or slightly smaller dimension than the dimension of the outer shape of the corneal endothelial layer. Preferably, "slightly" described here, means a range of the dimension of 0.2 to 1.0 mm.

The base end side of the supporting portion 50 is gradually narrowed. However, a partially wider protruding portion 52 is formed in the vicinity of the base end portion of the supporting portion 50. The protruding portion 52 has a function of making a propensity of the shape of the supporting portion 50 or retaining its shape.

Figure 9:
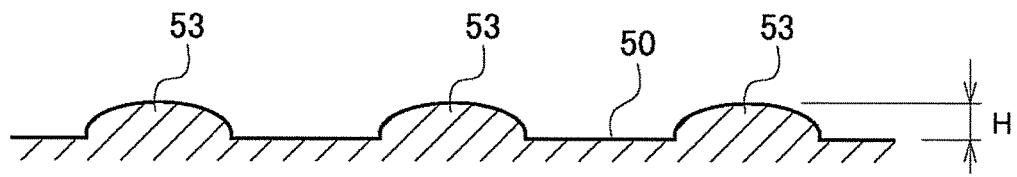
FIG. 9 is a sectional view of a supporting portion of the support member in a width direction.

As illustrated in FIG. 9, a plurality of protrusions 53 is formed on the surface of the supporting portion 50. Each protrusion 53 is formed so as to be elongated straight in a planar direction of the supporting portion 50. Each protrusion 53 is formed having a protruding dimension (height) H of about 0.10 mm for example, with a surface of the supporting portion 50 (surface on the side supporting the corneal endothelial layer) as a reference surface.

In the explanation given hereafter, protrusions 53 formed in an almost half of the region closer to the supporting portion 50 are called tip side protrusions 53a, and protrusion 53 formed in an almost half of the region closer to the rear end of the supporting portion 50 are called rear end side protrusions 53b.

The tip side protrusions 53a are formed in a direction parallel to the central axis direction of the supporting member 25. A plurality of (seven in the figure) tip side protrusions 53a are formed side by side at a constant interval in a width direction of the supporting portion 50. On the other hand, three protrusions are formed as the rear end side protrusions 53b. Rear end side protrusion 53b-1 positioned on the central axis of the supporting member 25 is formed in a direction parallel to the central axis direction of the supporting member 25, and two rear end side protrusions 53b-2 at both sides of the rear end side protrusion 53b-1 are formed in a state of being inclined at a prescribed angle with respect to the central axis of the supporting member 25. The both sides two rear end side protrusions 53b-2 are formed at right and left sides as a pair so as to sandwich the rear end side protrusion 53b-1. Further, the both sides two rear end side protrusions 53b-2 are arranged obliquely in a direction along approximately V-shape so that an interval between both portions becomes gradually larger toward the tip side from the rear end side of the supporting portion 50.

Base Portion

The base portion 51 is the portion that does not relatively move with respect to the holding member 24, but relatively moves with respect to the nozzle member 23, when the nozzle member 23 is relatively moved with respect to the holding member 23. The base portion 51 is formed into an oval shape similarly to the cross-sectional shape of the space 33 in the cylindrical portion 30, viewed from the central axis direction. The base portion 51 is a hollow member having a circular hole portion 56a and an oval-shaped hole portion 56b on the same axis. The hole portion 56a is formed on the rear end side of the base portion 51, and the hole portion 56b is formed on the tip side of the base portion 51. The hole portion 56b is formed so that the width of the hole (long axis dimension) becomes larger toward the tip side from the rear end side of the base portion 51. The abovementioned supporting portion 50 is disposed closer to one end side in a short axis direction of the base portion 51, so as not to close the hole portion 56b.

On the other hand, a groove portion 57 is formed on the outer circumference of the base portion 51. The groove portion 57 is the portion for attaching the sealing member 26 described later to the base portion 51. The outer shape of the base portion 51 where the groove portion 57 is formed, is not the oval shape but a circular shape.

Sealing Member

Figure 10A:
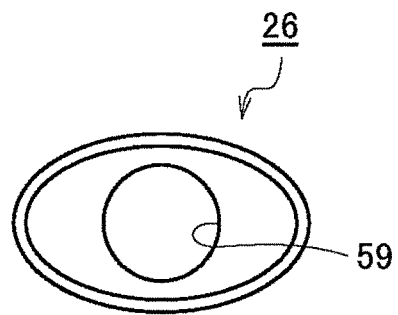
FIGS. 10A, 10B and 10C are front end, side and lower side views of a sealing member.
Figure 10B:
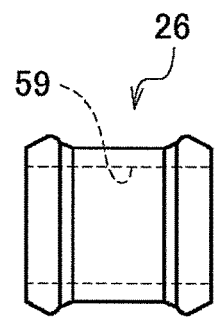
Figure 10C:
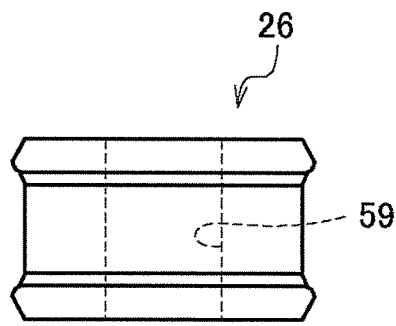

FIGS. 10A, 10B and 10C illustrate a configuration of the sealing member, wherein FIG. 10A is a front view, FIG. 10B is a side view, and FIG. 10C is a lower side view.

The sealing member 26 is made of, for example, synthetic rubber such as silicone rubber or fluorine rubber, etc. The sealing member 26 is a hollow member having a hole 59. An outer shape of the sealing member 26 is an oval shape similarly to the outer shape of the base portion 51. The shape of the hole 59 is formed into a circular shape corresponding to an outer circumferential shape of the portion where the groove portion 57 of the base portion 51 is formed. The sealing member 26 constitutes a plug by being mounted on the groove portion 57 of the base portion 51. Namely, when the nozzle member 23 is relatively moved with respect to the holding member 24, the outer circumferential surface of the nozzle member 26 is maintained in a tight contact with an inner circumferential surface of the cylindrical portion 30, whereby the sealing member 26 serves as the plug.

Needle Member

Figure 11A:
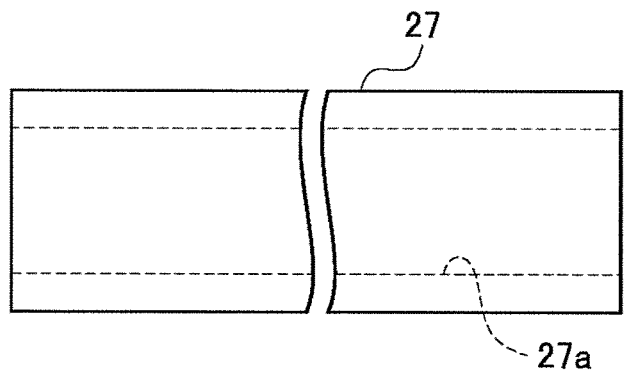
FIGS. 11A and 11B are side and front end views of a needle member.
Figure 11B:
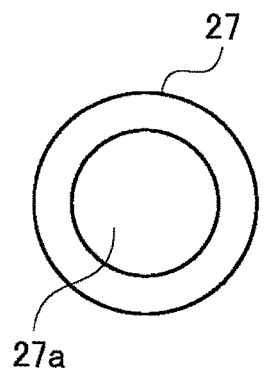

FIGS. 11A and 11B illustrate a configuration of a needle member, wherein FIG. 11A is a side view, and FIG. 11B is a view viewed from a central axis direction (or "front end view").

The needle member 27 is a metal elongated cylindrical portion. As a constituent material of the needle member 27, preferably stainless steel such as SUS 304, etc., can be used. The needle member 27 is formed into a straight shape having an axial hole 27a. An outer diameter of the needle member 27 is set to a dimension corresponding to a diameter of the hole portion 56a of the base portion 51. Both ends of the needle member 27 are cut into a flat shape vertical to the central axis direction respectively.

Connecting Member

Figure 12A:
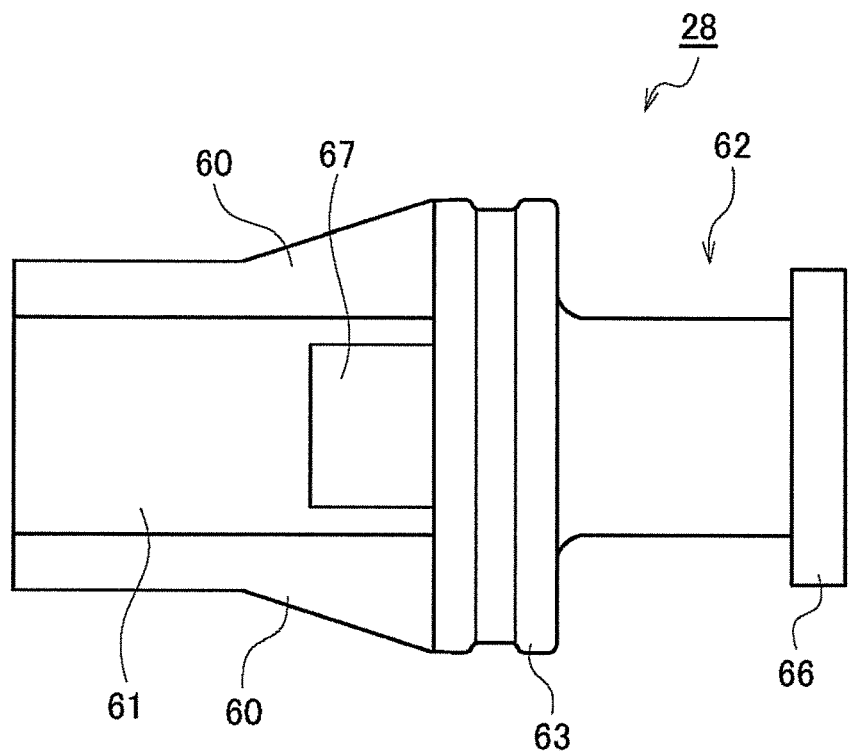
FIGS. 12A and 12B are plan and side views of a connecting member.
Figure 12B:
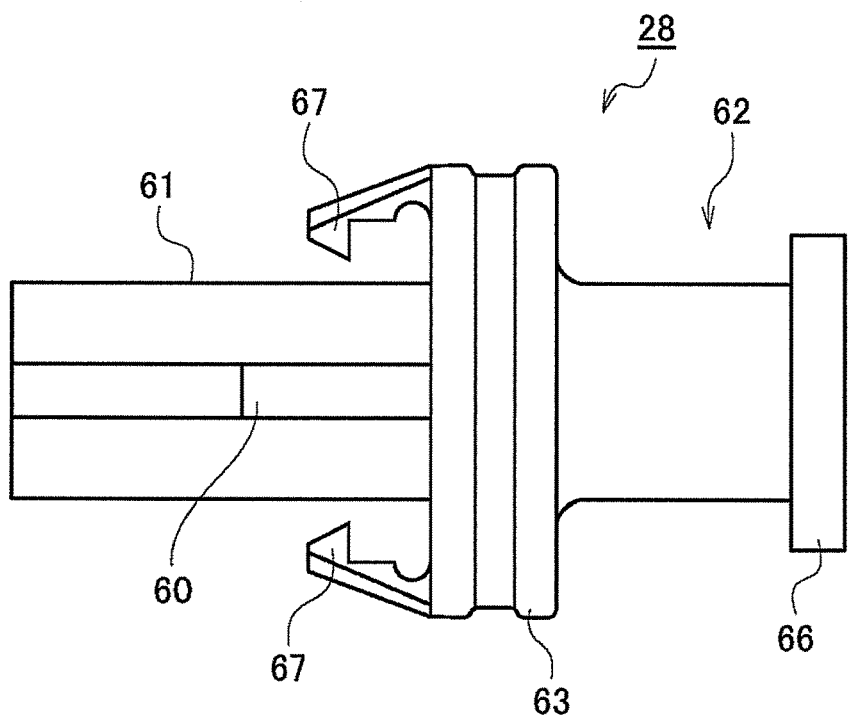
Figure 13A:
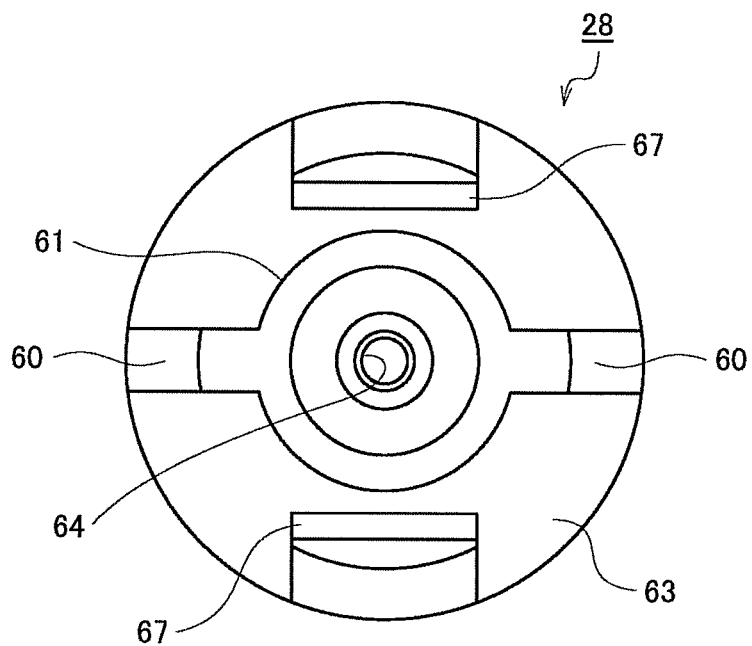
FIGS. 13A and 13B are front end and rear end views of the connecting member.
Figure 13B:
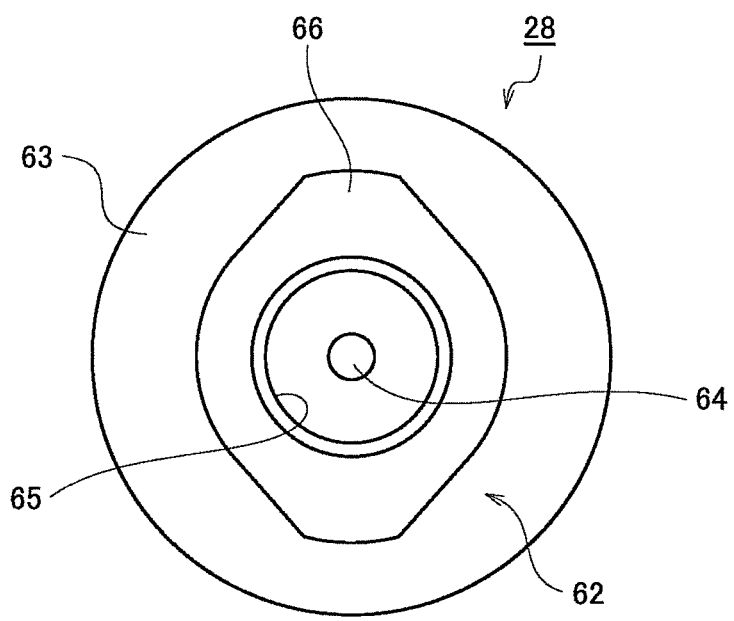

FIGS. 12A and 12B illustrate a configuration of a connecting member, wherein FIG. 12A is a plan view and FIG. 12B is a side view. Further, FIG. 13A is a view of the connecting member viewed from a tip side (or "front end view"), and FIG. 13B is a rear end view.

The connecting member 28 is the member for connecting the syringe unit 22 to the body unit 21. The connecting member 28 is the member obtained by the integral molding of resin such as polypropylene for example. The connecting member 28 has roughly integrally a needle connecting portion 61, a syringe connecting portion 62, and an engaging portion 63.

Needle Connecting Portion

The needle connecting portion 61 is formed into a cylindrical shape. A through hole 64 is formed on the needle connecting portion 61. A hole diameter of the through hole 64 is set to be gradually smaller toward the rear end side from the tip side of the connecting member 28, whereby the through hole 64 becomes a stepped hole. Further, the hole diameter of the through hole 64 is set so as to correspond to the outer diameter of the needle member 27. A pair of stopper pieces 60 is formed on the outer circumferential surface of the needle connecting portion 61. A pair of stopper pieces 60 is arranged at right and left sides as a pair viewed from the central axis direction of the connecting member 28. Each stopper piece 60 is engaged with the slit 43 of the holding member 24 in a state that the connecting member 28 is mounted on the rear end portion of the holding member 24.

Syringe Connecting Portion

The syringe connecting portion 62 is formed into a cylindrical shape. A through hole 65 is formed on the syringe connecting portion 62. The through hole 65 is spatially connected to the through hole 64 of the needle connecting portion 61 in the central axis direction of the connecting member 28. The hole diameter of the through hole 65 is set to be larger than the hole diameter of the through hole 64 of the needle connecting portion 61. The hole diameter of the through hole 65 is set to a dimension corresponding to the outer diameter of an insertion portion 76 of a syringe 74 described later. Further, the hole diameter of the through hole 65 is set to be continuously smaller toward the tip side from the rear end side of the connecting member 61. A protruding portion 66 for Luer lock described later, is formed on the rear end portion of the syringe connecting portion 62. The protruding portion 66 is formed in a state of protruding in a diameter direction of the syringe connecting portion 62. Further, the protruding portion 66 is formed substantially in the oval shape viewed from the central axis direction of the connecting member 28.

Engaging Portion

The engaging portion 63 is formed into a flange shape at a joint part between the needle connecting portion 61 and the syringe connecting portion 62. A pair of locking claws 67 is formed on the engaging portion 63. The pair of locking claws is formed at a position where the phase is shifted by 90° from the abovementioned pair of stopper pieces 60 in a circumferential direction around the central axis of the connecting member 28. Each locking claw 67 has a suitable flexibility, and is formed in a state of protruding toward the tip side of the connecting member 28. Each locking claw 67 is adapted to be locked in a pair of locking holes 47 formed on the holding member 24.

Pressing Member

FIGS. 14A, 14B and 14C illustrate a configuration of a pressing member, wherein FIG. 14A is a plan view, FIG. 14B is a rear end view and FIG. 14C is a side view.

The pressing member 29 is the member used for pressing an iris 6 (see FIG. 1) as needed, in performing surgery of corneal endothelium transplantation (for preventing iris prolapse). The pressing member 29 is obtained by integral molding of resin for example, and has a pressing portion 70 extending in a thin plate shape, a support piece 71 thicker than the pressing portion 70, a pillar portion 72 protruding from an end portion of the support piece 71 in a thickness direction, and a hook portion 73 formed on a protruding end of the pillar portion 72. The pressing portion 70 is inserted into an eye in performing surgery of corneal endothelium transplantation, so as to press the iris 6. The support piece 71 is adapted to support the pressing portion 70, and extends integrally with the pressing portion 70. A thickness dimension of the support piece 71 is uniform at a side where the pillar portion 72 is formed, but becomes gradually thicker toward the pillar portion 72 from a boundary between the pressing portion 70 and the support piece 71. The pillar portion 72 is adapted to move along the guide groove 38 while engaging with the guide groove 38 formed on the holding member 24. The hook portion 73 is adapted to be hooked on the guide groove 38 through the through hole 39 formed on the holding member 24. Therefore, the hook portion 73 is formed into a smaller circular shape than a hold diameter of the through hole 39.

Configuration of a Syringe Unit

As illustrated in FIG. 3, the syringe unit 22 is configured using a syringe 74 and a plunger 75. The syringe unit 22 has a function as a positive pressure generator for generating a positive pressure in the cylindrical portion 30 to push-out the therapeutic agent stored in the cylindrical portion 30 together with the supporting portion 50, to outside the cylindrical portion 30, through the opening 34 of the nozzle member 23. The syringe 74 is formed into a cylindrical shape as a whole. An insertion portion 76 and an internal threaded portion 77 are provided on the tip of the syringe 74. The insertion portion 76 is formed in a hollow configuration communicating with a hollow part of the syringe 74. The insertion portion 76 is the portion inserted into the through hole 65 of the syringe connecting portion 62. The internal threaded portion 77 is formed into a cylindrical shape in a state of surrounding the insertion portion 76. A screw is formed in a spiral shape, on an inner peripheral surface of the internal threaded portion 77. The inner threaded portion 77 constitutes a luer lock connector together with the syringe connecting portion 62. A flange 78 is provided on the rear end of the syringe 74.

The plunger 75 has a sliding portion 80 made of rubber, and a rod portion 81 supporting the sliding portion 80. The sliding portion 80 is formed on the tip of the plunger 75. The sliding portion 80 moves toward the central axis of the syringe 74 by pulling or pushing movement (operation) of the rod portion 81, while in tight contact with the inner peripheral surface of the syringe 74. The rod portion 81 is assembled into the syringe 74 so as to be inserted and removed thereinto/therefrom. The tip side of the rod portion 81 is inserted into the syringe 74 together with the sliding portion 80. The rear end side of the rod portion 81 is disposed in a state of protruding from the syringe 74. Further, a flange member 82 is formed on the rear end part of the rod portion 81.

3. Method of Manufacturing the Therapeutic Instrument (Assembly Procedure)

A method of manufacturing the therapeutic instrument according to a first embodiment of the present invention will be described next.

The therapeutic instrument 20 has the body unit 21 and the syringe unit 22, but the syringe unit 22 is not required to be a dedicated component, and may be a ready-made component. Here, as an example, the ready-made component is used as the syringe unit 22. In this case, an assembly process of the body unit 21 substantially corresponds to a manufacturing process of the therapeutic instrument 20. A specific procedure of the assembly process of the body 21 will be described hereafter.

First, the tip part of the needle member 27 is inserted into the base portion 51 of the support member 25 so as to be fixed thereto using an adhesive agent, etc. Next, the sealing member 26 is attached to the groove portion 57 of the base portion 51, an assembly component as illustrated in FIG. 15 is thus obtained. In this assembly component, the sealing member 26 is attached to the groove portion 57 of the base portion 51, and therefore the sealing member 26 is hardly peeled-off from the base portion 51 during use of the therapeutic instrument 20 described later. The sealing member 26 may be attached to the groove 57 before the needle member 27 is attached to the support member 25. Next, the rear end portion of the needle member 27 is inserted into the through hole 64 of the connecting member 28 so as to be fixed thereto using the adhesive agent, etc.

Next, the support member 25 and the needle member 27 are inserted into the space 33 of the cylindrical portion 30 through the opening 35 on the rear end side of the nozzle member 23. At this time, the direction of the supporting portion 50 is set as follows. That is, the direction of the supporting portion 50 is set in a direction so that the protruding portion 52 of the supporting portion 50 is disposed along an inner surface of the beak portion 36 at the side where an edge of the obliquely cut opening 34 is largely protruded frontward, when the supporting portion 50 is protruded from the opening 34 of the tip of the beak portion 36. In this case, even in a state that the supporting portion 50 is protruded from the opening 34 of the tip of the beak portion 36, the protruding portion 52 of the supporting portion 50 remains to be stored in the cylindrical portion 30. In this state, the protruding portion 52 is curved along the inner circumferential surface of the cylindrical portion 30, and therefore the supporting portion 50 is also retained in a slightly curved shape following a curved shape of the protruding portion 52.

Next, the pressing member 29 is set in the hollow part 40 of the holding member 24. At this time, the pressing member 29 is inserted into the hollow part 40 from the opening 41 on the tip side of the holding member 24. Further, the hook portion 73 of the pressing member 29 is inserted into the through hole 39 from the inner circumferential side of the holding member 24, and in this state, the pressing member 29 is slightly moved to the tip side, to thereby allow the pillar portion 72 of the pressing member 29 to pass through the guide groove 38 of the holding member 24.

Next, the cylindrical portion 30 of the nozzle member 23 is inserted into the hollow part 40 from the opening 42 at the rear end side of the holding member 24. At this time, the wing portions 37 protruded at both sides of the nozzle member 23, and stopper pieces 60 protruded at both sides of the guide groove 38, are respectively inserted into corresponding slits 43 of the of the holding member 24. Further, a pair of locking claws 67 vertically formed on the connecting member 28, are locked on the locking holes 47 at a place where notches 48 are formed on the holding member 24. Accordingly, the connecting member 28 is set in a fixed state to the rear end portion of the holding member 24. Further, in the hollow part 40 of the holding member 24, the pressing member 70 and the support piece 71 of the pressing member 29 are set in a sandwiched state between the inner circumferential surface of the holding member 24 and the outer circumferential surface of the cylindrical portion 30 of the nozzle member 23.

In such an assembled state of the body unit 21, the holding member 24 and the nozzle member 23 are supported so as to be relatively movable in the central axis direction. When a force is actually added to move the nozzle member 23 and the holding member 24, both of them are relatively moved while undergoing a sliding frictional resistance of the sealing member 26 in contact with the inner circumferential surface of the cylindrical portion 30. A moving range of the nozzle member 23 with respect to the holding member 24, is limited to a state in which the wing portions 37 of the nozzle member 23 abut on the stopper pieces 60, from a state in which the wing portions 37 of the nozzle member 23 abut on the tips of the slits 43. In a state of moving the nozzle member 23 to a most distant side of the tip, the cylindrical portion 30 is set in a largely protruded state from the opening 41 of the holding member 24, and in a state in which the whole part of the supporting portion 25 is housed in the space 33 of the cylindrical portion 30. In a state in which the nozzle member 23 is moved to a most distant side of the rear end, the beak portion 36 of the cylindrical portion 30 is set in a protruded state from the opening 41 of the holding member 24, and in a state in which the supporting portion 50 of the supporting member 25 is largely protruded to outside through the opening 34 of the cylindrical portion 30. At this time, a rotational movement of the nozzle member 23 is regulated by an engagement of the wing portions 37 of the nozzle member 23 and the slits 43 of the holding member 24.

Further, the pressing member 29 is movably supported in the central axis direction of the holding member 24, separately from the relative movement of the nozzle member 23 and the holding member 24. The moving range of the pressing member 29 is limited in a range of a state in which the hook portion 73 of the pressing member 29 is positioned in the vicinity of the through hole 39, from a state in which the hook portion 73 of the pressing member 29 abuts on the tip of the guide groove 38. In a state in which the pressing member 29 is moved at a most distant side of the tip, the whole part of the pressing portion 70 is set in a protruded state from the opening 41 of the holding member 24. Further, in a state of moving the pressing member 29 at the most distant side of the rear end, only the tip of the pressing member 70 is set in a protruded state from the opening 41 of the holding member 24.

Figure 16A:
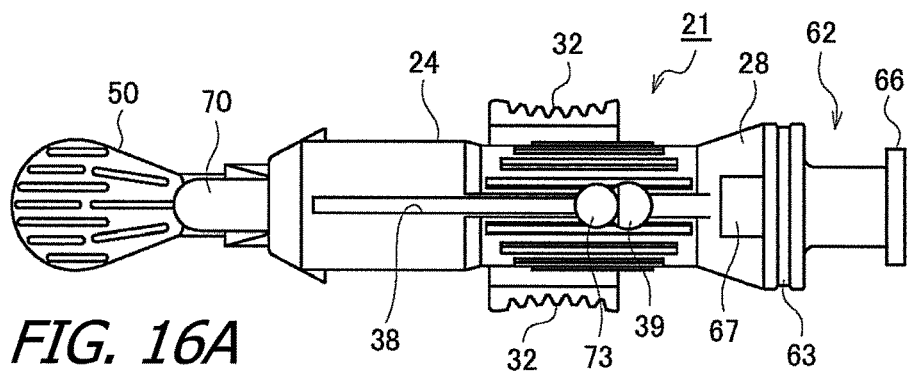
FIGS. 16A and 16B are plan and side cross-sectional views of a body unit after completion of the assembly.
Figure 16B:
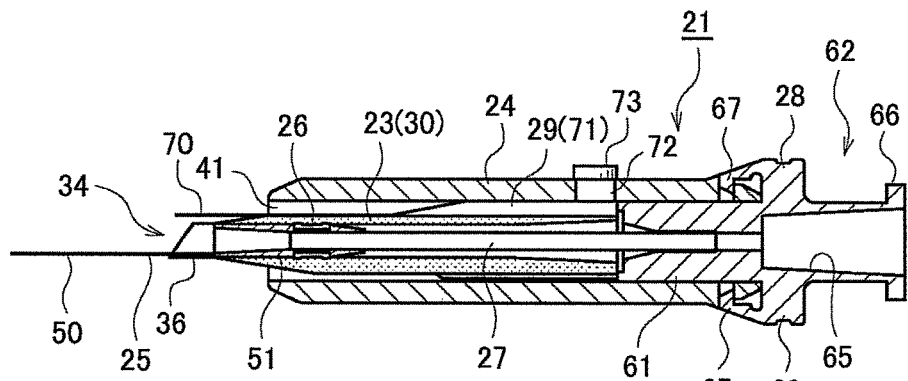

As described above, the assembly of the body unit 21 is completed. FIGS. 16A and 16B illustrate a state of the body unit 21 after completion of the assembly. When the therapeutic instrument 20 is actually used, the syringe unit 22 is attached to the body unit 21 during use of the therapeutic instrument 20. Specifically, the syringe 74 is rotated so that the tip part of the syringe 74 is slightly pressed against the syringe connecting portion 62 of the connecting member 28 fixed to the rear end of the holding member 24. Then, the insertion portion 76 of the syringe 74 is gradually inserted into a depth side of the through hole 65 while the protruding portion 66 of the syringe connecting portion 62 and the internal threaded portion 77 of the syringe 74 are screwed together. At this time, the tip of the insertion portion 76 of the syringe 74 abuts on the depth side of the through hole 65, and in this state, the syringe 74 is rotated until a suitable resistance is generated. Thus, the hole 27a of the needle member 27 and the hollow part of the syringe 74 are set in a spatially connected state.

The syringe unit 22 may be attached to the body unit 21 in a state in which the plunger 75 is attached to the syringe 74, or in a state in which the plunger 75 is removed from the syringe 74.

4. Method of Using the Therapeutic Instrument

A method of using the therapeutic instrument according to a first embodiment of the present invention will be described next. Regarding the method of using the therapeutic instrument 20, first, a basic operation of the therapeutic instrument 20 will be described, and actually how to use the therapeutic instrument 20 in the corneal endothelium transplant surgery will be described thereafter.

Basic Operation

As illustrated in FIGS. 16A and 16B, the supporting portion 50 of the support member 25 is largely protruded state from the tip of the cylindrical portion 30 of the nozzle member 23, in a state of moving the nozzle member 23 to the most distant side of the rear end of the holding member 24. Further, the tip of the pressing portion 70 of the pressing member 29 is set in a protruded state from the tip of the holding member 24, in a state of moving the pressing member 29 to the most distant side of the rear end of the holding member 24. In this state, a protruding dimension of the tip of the pressing portion 70 and a protruding dimension of the tip (beak portion 36) of the cylindrical portion 30 are almost the same dimension, with the tip of the holding member 24 as a reference.

Figure 17A:
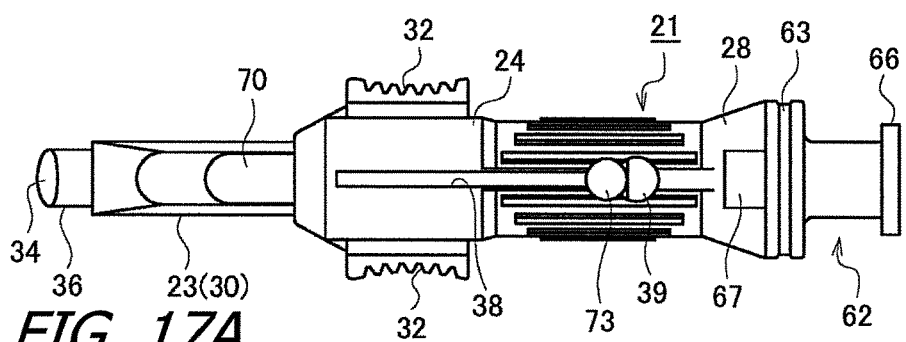
FIGS. 17A and 17B are plan and side cross-sectional views illustrating a basic operation of a therapeutic instrument.
Figure 17B:
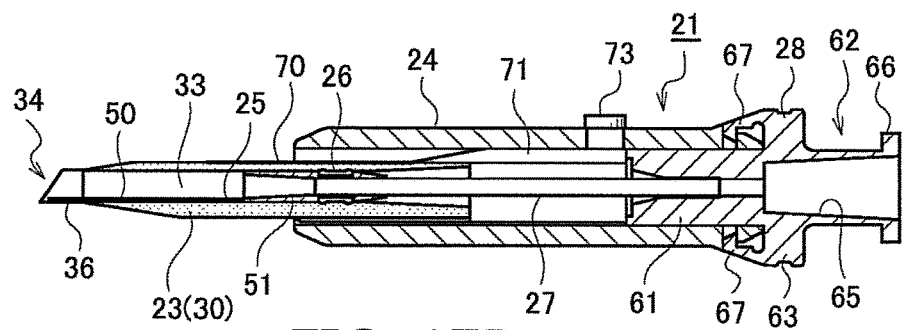

When the nozzle member 23 is moved to the tip side (referred to as an "advancement" hereafter) with respect to the holding member 24 from the state illustrated in FIGS. 16A and 16B, the supporting portion 50 of the support member 25 is gradually pulled in the cylindrical portion 30 in accordance with this movement. At this time, the supporting portion 50 of the support member 25 is gradually curved while in contact with the edge of the opening 34 of the tip of the cylindrical portion 30, and set in a deformed state into a roll shape finally (a rounded state into an arc shape). Then, as illustrated in FIGS. 17A and 17B, in a stage when the nozzle member 23 is set in a most advanced state, the supporting portion 50 of the support member 25 is completely housed in the cylindrical portion 30 of the nozzle member 23. In this state, the supporting portion 50 of the support member 25 is set in a deformed state into a roll shape, with a formation surface of the protrusion 53 disposed inside.

Further, when the nozzle member 23 is moved to the rear end side (referred to as "retreat" hereafter) with respect to the holding member 24, from a state illustrated in FIGS. 17A and 17B, the supporting portion 50 of the support member 25 is gradually protruded from the tip of the cylindrical portion 30, following the movement of the nozzle member 23. At this time, the supporting portion 50 of the support member 25 is gradually expanded into a planar shape from the state deformed into the roll-shape.

In an advancing movement and a retreating movement of the nozzle member 23, in any case, the sliding frictional resistance acts on a contact portion between the outer peripheral part of the sealing member 26 and the inner circumferential surface of the cylindrical portion 30. The magnitude of the sliding frictional resistance is adjusted to a frictional force such as not excessively inhibiting the relative movement of the nozzle member 23 and the holding member 24, using an outer dimension, etc., of the sealing member 26 as adjustment parameters. Then, owing to such a sliding frictional resistance, the nozzle member 23 and the holding member 24 can be stopped at an arbitrary position in the range of the relative movement, and such a stop state can be maintained.

Figure 18A:
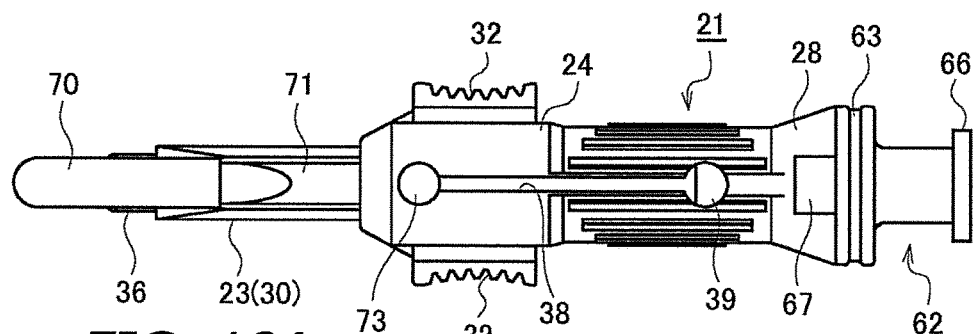
FIGS. 18A and 18B are additional plan and side cross-sectional views illustrating a basic operation of the therapeutic instrument.
Figure 18B:
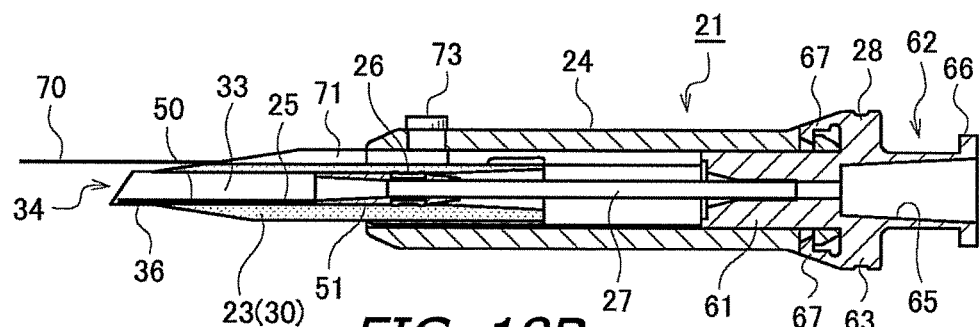

Further, when the pressing member 29 is moved with respect to the holding member 24, to the tip side (referred to as "advancement" hereafter) from a state illustrated in FIGS. 17A and 17B, the protruding dimension of the pressing portion 70 of the pressing member 29 becomes gradually increased, following the movement of the pressing member 29. Then, in a state when the pressing member 29 is most advanced, as illustrated in FIGS. 18A and 18B, the tip of the pressing portion 70 is set in a more largely protruded state than the tip of the cylindrical portion 30. When the pressing portion 70 is thus protruded, by making the support piece 71 which is thicker than the pressing portion 70, brought into contact with the edge of the opening 41 of the holding member 24, the support piece 71 is pressed against the cylindrical portion 30 of the nozzle member 23. Then, due to a mechanical contact resistance generated at this time, the movement of the pressing member 29 is suitably suppressed.

Further, when the pressing member 29 is moved with respect to the holding member 24, to the rear end side (referred to as "retreat" hereafter) from a state illustrated in FIGS. 18A and 18B, the protruding dimension of the pressing portion 70 of the pressing member 29 is gradually decreased, following the movement of the pressing member 29. Then, when the pressing member 29 is set in a most retreated state, the state of the therapeutic instrument is returned to the state illustrated in FIGS. 17A and 17B.

Explanation is given here, with a basic operation of the therapeutic instrument 20 divided into several operations, but the basic operation performed when the therapeutic instrument 20 is actually used in the ophthalmic surgery is a part of the several operations, as described hereafter in a method of using the therapeutic instrument.

(Method of Using the Therapeutic Instrument)

A method of using the therapeutic instrument 20 will be described next. The method of using the therapeutic instrument 20 is roughly divided into a storage process and a pushing process in time series. Each process will be more specifically described hereafter.

Storage Process

First, as illustrated in FIGS. 16A and 16B, the nozzle member 23 is set in a most retreated state, as a state of the body unit 21. In this state, the supporting portion 50 of the support member 25 is largely protruded in a planarly expanded state, from the tip of the cylindrical portion 30 of the nozzle member 23. On the other hand, as a state of the syringe unit 22, the inside of the syringe 74 is filled with a medical water in advance. Filling of the medical water is performed, for example, in such a manner that the insertion portion 76 of the syringe 74 is inserted into the medical water prepared by putting it in a vessel, etc., before the syringe unit 22 is attached to the body unit 21, and the plunger 75 is operated so as to be retracted. Thus, the medical water is sucked in the syringe 74 through the insertion portion 76. Therefore, the syringe unit 22 is attached to the body unit 21 in a state in which a prescribed amount of medical water is sucked in the syringe 74 by retraction of the plunger 75.

The medical water described in this specification, refers to a water suitable for a medical use, such as a sterilized water or saline, etc., for example. In the ophthalmic surgery, the medical water is used as an irrigation water. The medical water for filing the syringe 74, acts as an auxiliary role when setting the inside of the cylindrical portion 30 to a negative pressure or a positive pressure. However, instead of the medical water, gas such as air can be used.

Next, the inside of the cylindrical portion 30 of the nozzle member 23 is filled with the medical water, by pushing the syringe 74 of the syringe unit 22 by a prescribed amount.

Figure 19:
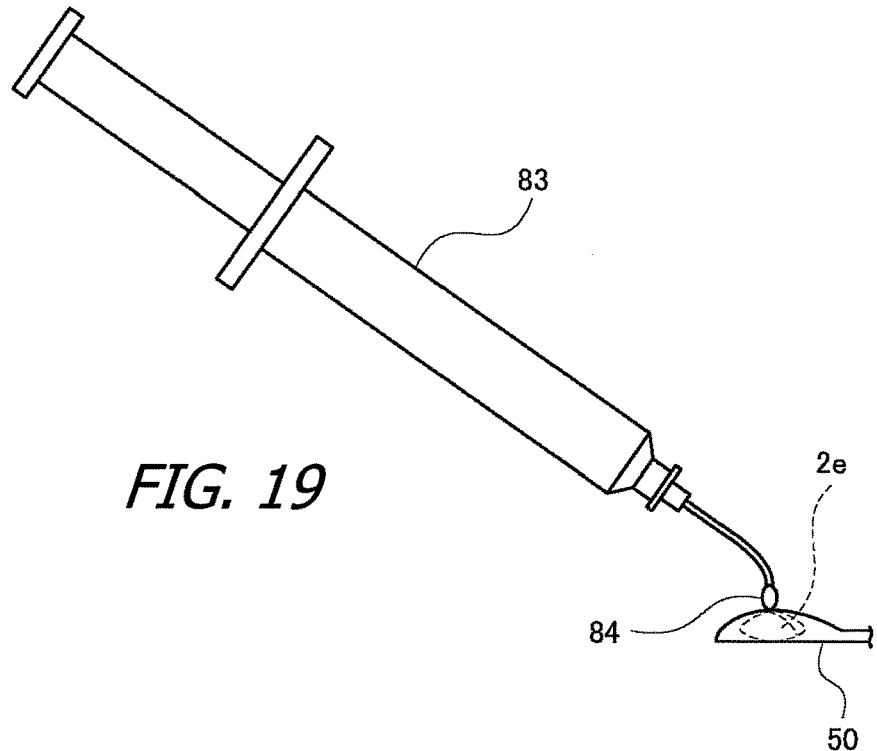
FIG. 19 is a view illustrating a method of using the therapeutic instrument.

Next, as illustrated in FIG. 19, the previously prepared corneal endothelial layer 2e is placed on the supporting portion 50. At this time, the corneal endothelial layer 2e is placed on each protrusion 53, on the surface of the supporting portion 50. Therefore, the corneal endothelial layer 2e is supported by each protrusion 53 in a slightly floated state from the surface of the supporting portion 50.

Next, as illustrated in FIG. 19, a liquid 84 is fed (dropped) on the corneal endothelial layer 2e on the supporting portion 50 using a dispenser 83. The abovementioned medical water may be used as the liquid 84 fed to the corneal endothelial layer 2e, but preferably, a higher viscoelastic material (viscoelastic material) than the medical water is more preferable. Further, hyaluronic acid can be given as a preferable example of the viscoelastic material. When the liquid of the viscoelastic material such as hyaluronic acid, etc., is fed to the corneal endothelial layer 2e, the surface of the corneal endothelial layer 2e is covered and protected by a viscoelastic property of the liquid. Therefore, a damage (such as a damage of a cell) received by the corneal endothelial layer 2e during the corneal endothelium transplant surgery, can be reduced.

Next, the supporting portion 50 is housed in the space 33 of the cylindrical portion 30, as illustrated in FIGS. 17A and 17B, by slowly advancing the nozzle member 23 so as not to add an excessive load on the corneal endothelial layer 2e on the supporting portion 50. Then, the supporting portion 50 is brought into contact with the edge of the opening 34 of the cylindrical portion 30 in a middle of the advancement of the nozzle member 23, and the supporting portion 50 is gradually deformed into U-shape under an outer force caused by such a contact. At this time, the corneal endothelial layer 2e is also deformed, similarly to the supporting portion 50. Further, when the nozzle member 23 is advanced, the negative pressure is generated in the cylindrical portion 30, due to an increase of a volume in the cylindrical portion 30 which is caused by existence of the sealing member 26 and the movement of the nozzle member 23. Therefore, the corneal endothelial layer 2e supported by the supporting portion 50 and the liquid 84 are housed in the space 33 of the cylindrical portion 30 so as to be sucked therein, by the generation of the negative pressure.

Thus, the corneal endothelial layer 2e is set in a completely housed state in the space 33 of the cylindrical portion 30. Further, the tip side of the cylindrical portion 30 is in a closed state by the liquid 84 sucked together with the corneal endothelial layer 2e.

Incidentally, regarding three rear end side protrusions 53b formed on the supporting portion 50, when two rear end side protrusions 53b-2 at both sides are arranged obliquely in a shape opening out toward the tip side from the rear end side, the whole body of the supporting portion 50 can be deformed uniformly into the roll-shape without causing unnecessary strain on the rear end side of the supporting portion 50. This is because when the two rear end side protrusions 53b-2 at both sides are obliquely arranged, each rear end side protrusion 53b-2 functions like a rib, to thereby deform the rear end side of the supporting portion 50 so as to be rolled inward from outside in a width direction of the supporting portion 50. In addition, a plurality of (three in the figure) rear end side protrusions 53b exhibit an effect of rectifying a flow of the medical water fed from the syringe unit 22 side so as to be diffused in a width direction of the supporting portion 50, and forming a water flow in a wide range of a support region in which the corneal endothelial layer 2e is supported. Further, the tip side of the supporting portion 50 is also easily rounded into a roll-shape, because a plurality of protruding tip side protrusions 53a extending in the central axis direction of the support member 25, are provided side by side on the whole body of the supporting portion 50 in the width direction.

As described above, the storage process is completed. In the actual corneal endothelial layer transplant surgery, an eyeball to be transplanted is subjected to a surgical operation for removing and inserting the corneal endothelial layer, and an eyeball having a corneal disease is subjected to a surgery of removing the corneal endothelial layer, before the above-mentioned storage process. Further, slit-like incisions are formed at two places of the cornea part by this surgical operation. Then, a suitable amount of the medical water (irrigation water) is continuously fed from one of the incisions, to thereby keep a cornea portion in a protruding bowl-shape.

Pushing Process

Next, a pushing process will be described. In the pushing process, first, the therapeutic instrument 20 that has already undertone the storage process in which the corneal endothelial layer 2e is housed in the tool body, is approached to the affected area of the eye (transplant site of the corneal endothelial layer). At this time, the therapeutic instrument 20 is approached to the eyeball, with the opening 34 directed toward the eyeball, the opening 34 being formed obliquely on the tip of the cylindrical portion 30.

Next, the tip of the nozzle member 23 is inserted into a cornea portion of the eyeball, with the therapeutic instrument 20 suitably inclined. Specifically, the beak portion 36 of the cylindrical portion 30 is inserted into the other incision formed on the cornea portion by the surgical operation. At this time, the hook portion 73 of the pressing member 29 is disposed to be directed to a face side of a patient.

Here, when prolapse of the iris (protrusion from the incision) likely to occur in the patient undergoing the corneal endothelial layer transplant surgery, as is often observed in a patient who suffers from intraoperative iris hypotonia syndrome, the pressing member 29 is advanced as illustrated in FIGS. 18A and 18B, before the therapeutic instrument 20 is approached to the eyeball. Then, when the therapeutic instrument 20 is approached to the eyeball, the beak portion 36 of the nozzle member 23 is inserted in the incision, while pressing the iris by inserting the pressing portion 70 of the pressing member 29 into the incision of the cornea portion. Thus, the prolapse of the iris can be prevented during the corneal endothelial layer transplant surgery.

Figure 20:
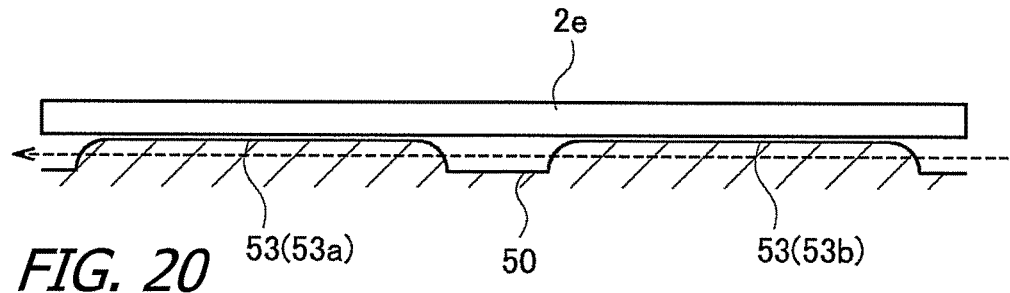
FIG. 20 is a view illustrating an example of forming a water flow.

Next, the plunger 75 is pushed-in by one hand, while keeping the therapeutic instrument 20 by the other hand. Then, the positive pressure acts on the space 33 of the cylindrical portion 30 due to the push-in of the plunger 75. Further, when the plunger 75 is pushed-in, the medical water in the syringe 74 is spat out by receiving the pushing force, into the cylindrical portion 30 through the needle member 27 and the base portion 51. At this time, the medical water flows toward the tip side from the rear end side of the supporting portion 50, through the hole portions 56a, 56b of the base portion 51. Further, the corneal endothelium layer is supported by a plurality of protrusions 53 in a floating state on the surface of the supporting portion 50, and therefore the medical water partially flows to a portion (gap portion) where the supporting portion 50 and the corneal endothelium layer 2e are faced each other, as shown by a broken arrow in FIG. 20. This reveals that a plurality of protrusions 53 has a function of introducing the medical water fed into the cylindrical portion by operating the syringe unit 22, to the place where the supporting portion 50 and the corneal endothelium layer 2e are faced each other, and owing to this function, a water flow is formed at the place where the supporting portion 50 and the corneal endothelium layer 2e are faced each other. Accordingly, even if there is a considerable elapse of time after the corneal endothelium layer 2e and the supporting portion 50 are in contact each other in the cylindrical portion 30, the corneal endothelium layer 2e can be surely separated from the supporting portion 50. Therefore, the corneal endothelium layer 2e is pushed-out from the tip (opening 34) of the beak 36 together with the liquid 84, by application of the positive pressure described above.

By the abovementioned method, the corneal endothelium layer 2e is inserted into an interior of an anterior chamber 5 (see FIG. 1).

5. Effect of a First Embodiment

According to the therapeutic instrument 20 of a first embodiment of the present invention, when the plunger 75 is operated to be pushed-in, from a state in which the corneal endothelial layer 2e is housed in the cylindrical portion 30 of the nozzle member 23, the corneal endothelial layer can be surely separated from the supporting portion 50 utilizing the flow of the medical water (water flow) fed into the interior of the space of the cylindrical portion 30. Thus, even if the time for housing the corneal endothelial layer 2e in the cylindrical portion 30 becomes long, the corneal endothelial layer 2e can be smoothly pushed-out to outside the cylindrical portion 30. Accordingly, the corneal endothelial layer can be supplied (transplanted) into the cornea portion of the eyeball, without wasting an expensive corneal endothelial layer 2e. Further, an ophthalmologist who performs the corneal endothelium transplantation surgery, can proceed with an appropriate surgery with no risk of a failure in extruding the corneal endothelial layer 2e even when some work (such as an adjustment of an intraocular pressure) is required, after the abovementioned storage process is finished, and before the process is advanced to the pushing process.

6. Explanation for a Second Embodiment

The therapeutic instrument according to a second embodiment of the present invention is characterized particularly in the configuration of the supporting member 25, compared to a case of the abovementioned first embodiment. Explanation will be given hereafter.

Figure 21:
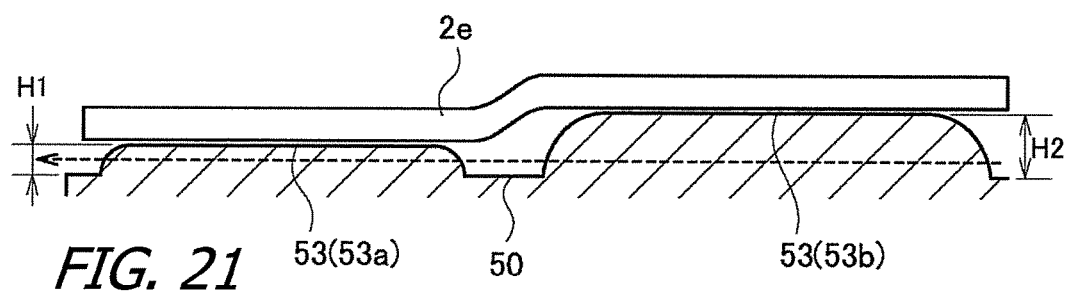
FIG. 21 is a cross-sectional view of an essential part illustrating the configuration of the support member included in the therapeutic instrument according to a second embodiment of the present invention.

FIG. 21 is a cross-sectional view of an essential part illustrating the configuration of the support member included in the therapeutic instrument according to a second embodiment of the present invention. In this embodiment, when a protruding dimension H1 of the tip side protrusion 53a and a protruding dimension H2 of the rear end side protrusion 53b are compared, the protruding dimension H2 of the rear end side protrusion 53b is set to be larger than the protruding dimension H1 of the tip side protrusion 53a. For example, the protruding dimension H1 of the tip side protrusion 53a is set to 0.08 mm, and the protruding dimension H2 of the rear end side protrusion 53b is set to 0.15 mm which is equivalent to twice the protruding dimension H2. Thus, the rear end side protrusion 53b is in a more largely protruded state than the tip side protrusion 53a, with a surface of the supporting portion 50 (surface on the side supporting the corneal endothelial layer) as a reference surface. In such a case, when the corneal endothelial layer 2e is placed on the supporting portion 50, the tip side protrusion 53a is brought into contact with the tip side of the corneal endothelial layer 2e, and the rear end side protrusion 53b is brought into contact with the rear end side of the corneal endothelial layer 2e. At this time, a posture of the corneal endothelial layer 2e supported by the supporting portion 50 is the posture with the rear end side of the corneal endothelial layer 2e raised (frontward inclined posture).

When the corneal endothelial layer 2e is supported by the supporting portion 50 in the abovementioned posture, and when the medical water is fed into the cylindrical portion 30 by the pushing operation of the plunger 75 in the pushing process described in the first embodiment, the rear end side protrusion 53b is positioned on an upstream side, and the tip side protrusion 53a is positioned on a downstream side, with respect to the flow of the medical water. At this time, by setting the protruding dimension H2 of the rear end side protrusion 53b positioned on the upstream side of the water flow, to be larger than the protruding dimension H1 of the tip side protrusion 53a positioned on the downstream side, the medical water fed into the cylindrical portion 30 easily flows to the place where the supporting portion 50 and the corneal endothelial layer 2e are faced each other. Further, by forming the posture in which the rear end side of the corneal endothelial layer 2e is raised (frontward inclined posture), the corneal endothelial layer 2e has an appropriate inclination with respect to an advancing direction of the medical water flowing along the surface of the supporting portion 50. Therefore, on the place where the supporting portion 50 and the corneal endothelial layer 2e are faced each other, the medical water flowing to this portion acts to push-out the corneal endothelial layer 2e under the positive pressure (pressing force) caused by operating the plunger 75. Accordingly, the corneal endothelial layer 2e can be forcibly pushed-out utilizing the flow of the medical water (water flow) fed into the space 33 of the cylindrical portion 30.

When there are a plurality of rear end side protrusions 53b on the rear end side of the supporting portion 50, not all of the protruding dimensions of the rear end side protrusions 53b are required to be set to be large, but only a part of the protruding dimensions of the rear end side protrusions 53b may be set to be large so as to raise the rear end side of the corneal endothelial layer 2e supported by the supporting portion 50.

Further, the protruding dimensions of the rear end side protrusions 53b of the supporting portion 50 may set to be gradually larger toward the rear end side (as approaching the rear end side of the supporting portion 50) from the tip side of the supporting portion 50. Further, when a plurality of (multiple numbers of) protrusions are formed on the supporting portion 50 in a dot-like arrangement, there may be a difference in the protruding dimensions of the protrusions between the tip side and the rear end side of the supporting portion 50, or the protruding dimension of each protrusion may be set to be gradually larger toward the rear end side from the tip side.

7. Explanation for a Third Embodiment

The therapeutic instrument according to a third embodiment of the present invention, is characterized particularly in the configuration of the nozzle member 23 and the supporting member 25, compared to the case of the first embodiment. Explanation will be given hereafter.

Figure 22:
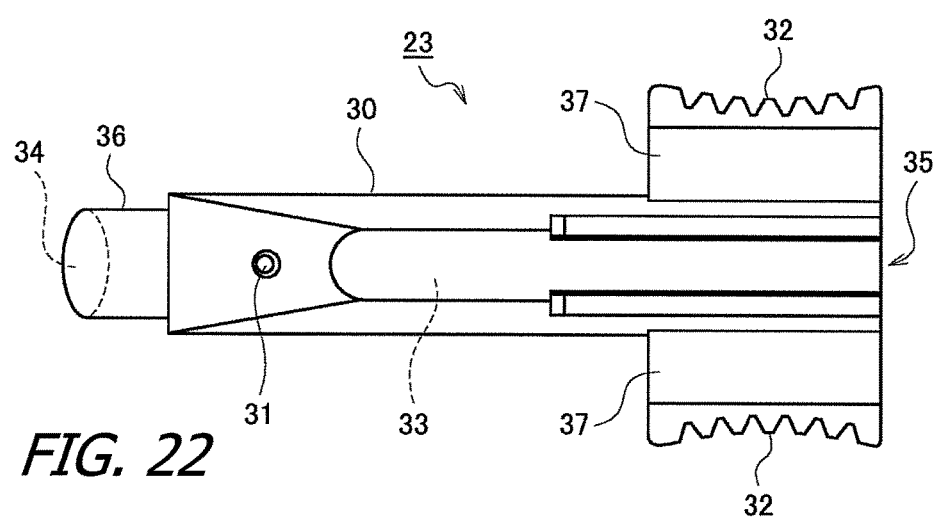
FIG. 22 is a lower side view illustrating the configuration of the nozzle member included in the therapeutic instrument according to a third embodiment of the present invention.
Figure 23:
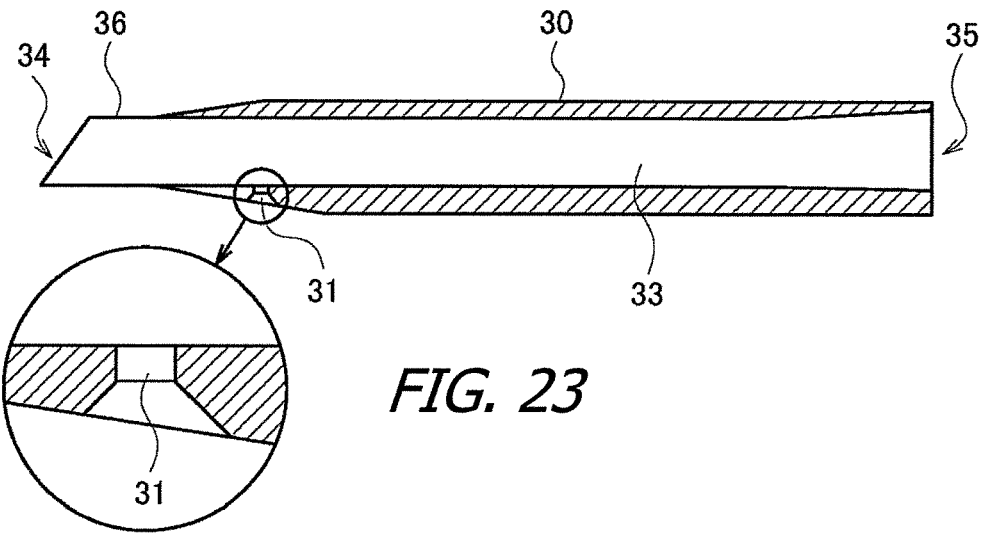
FIG. 23 is a side cross-sectional view illustrating the configuration of the nozzle member included in the therapeutic instrument according to the third embodiment of the present invention.

FIG. 22 is a lower side view illustrating the configuration of the nozzle member included in the therapeutic instrument according to the third embodiment of the present invention, and FIG. 23 is a side cross-sectional view. In this embodiment, a first through hole 31 is formed on the cylindrical portion 30 of the nozzle member 23. More specifically, the tip side upper and lower surfaces of the cylindrical portion 30 are inclined so as to be narrowed toward the beak portion 36 respectively, and a first through hole 31 is provided in the middle of one of the inclined surfaces. The first through hole 31 is communicated with the space 33 of the cylindrical portion 30.

Figure 24:
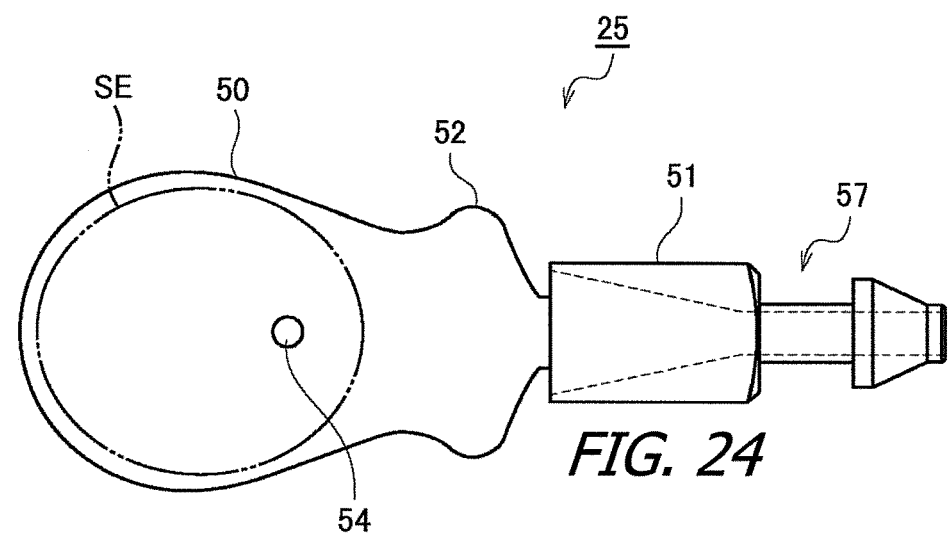
FIG. 24 is a planar view illustrating the configuration of the support member included in the therapeutic instrument according to a third embodiment of the present invention.

FIG. 24 is a planar view illustrating the configuration of the support member included in the therapeutic instrument according to the third embodiment of the present invention.

In this embodiment, a second through hole 54 is formed on the supporting portion 50 of the support member 25, corresponding to the first through hole 31. The second through hole 54 is provided in a support region SE of the supporting portion 50 in which the corneal endothelium layer is supported. Preferably, the second through hole 54 is provided at a position closer to the rear end than a center position of the support region SE in the support region SE in which the corneal endothelium layer is supported.

Figure 25:
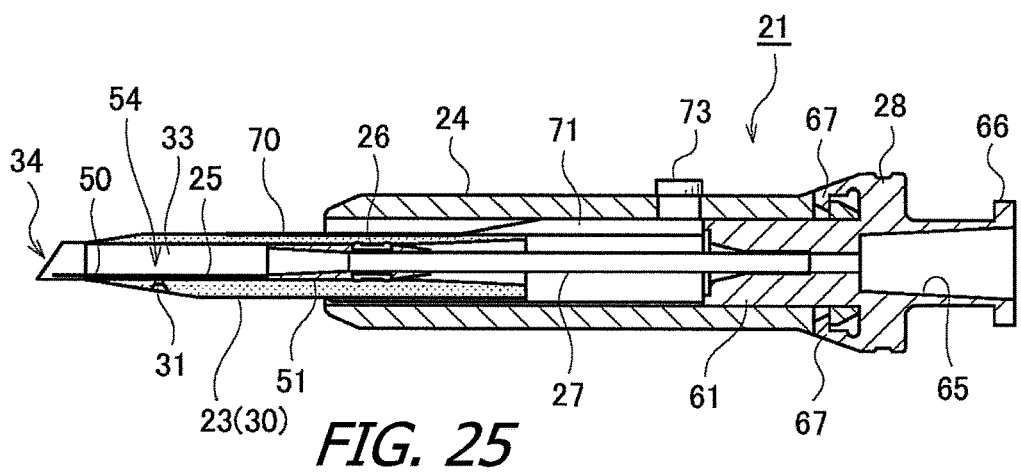
FIG. 25 is a view illustrating a positional relation between a first through hole and a second through hole.

As illustrated in FIG. 25, the first through hole 31 and the second through hole 54 are overlapped on each other when the nozzle member 23 is set in a most advanced state with respect to the holding member 24. Further, in the space 33 of the cylindrical portion 30, the second through hole 54 of the supporting portion 50 is disposed on the side where the first though hole 31 is formed. Each hole diameter of the first through hole 31 and the second through hole 54 may be set preferably in a range of 0.5 to 1.0 mm. Further, each hole diameter of the through holes 31 and 54 may be the same or may be different.

When the therapeutic instrument 20 according to the third embodiment of the present invention is used, the following state is made in the storage process described in the first embodiment. When the nozzle member 23 is most advanced so as to suck the corneal endothelial layer 2e supported by the supporting portion 50 into the cylindrical portion 30 by the negative pressure, as illustrated in FIG. 26A, the first through hole 31 and the second through hole 54 are overlapped on each other.

Figure 26A:
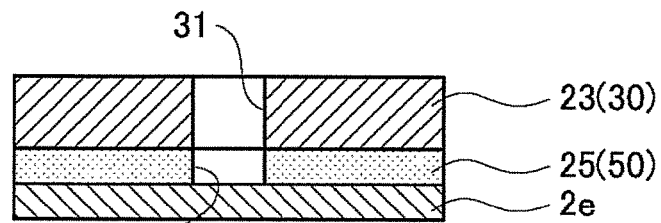
FIGS. 26A and 26B are a view illustrating other example of forming the water flow.
Figure 26B:
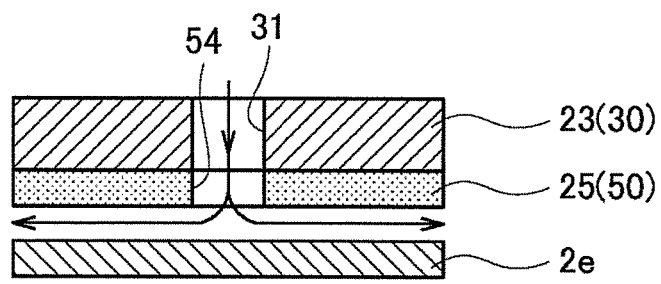

Therefore, in the pushing process thereafter, as illustrated in FIG. 26A, the first through hole 31 and the second through hole 54 are set in an overlapped state (state in which the nozzle member 23 is advanced), before the therapeutic instrument 20 is approached to the eyeball. Next, as illustrated in FIG. 26B, the medical water is injected into the cylindrical portion 30 through the first through hole 31 and the second through hole 54. For example, a thin tube is inserted into the first through hole 31, and injection of the medical water may be performed through this tube. At this time, as shown by the arrow in FIG. 26B, the medical water injected into the cylindrical portion 30 flows to the place where the supporting portion 50 and the corneal endothelial layer 2e are faced each other, to thereby form a water flow. Accordingly, even if the supporting portion 50 and the corneal endothelial layer 2e are stuck to each other, the supporting portion 50 and the corneal endothelial layer 2e are set in a separated (peeled-off) state by the formation of the water flow. Therefore, when the pushing operation of the plunger is performed, the corneal endothelial layer can be surely separated from the supporting portion 50, and can be pushed-out to outside of the cylindrical portion 30.

8. Explanation for a Fourth Embodiment

Figure 27:
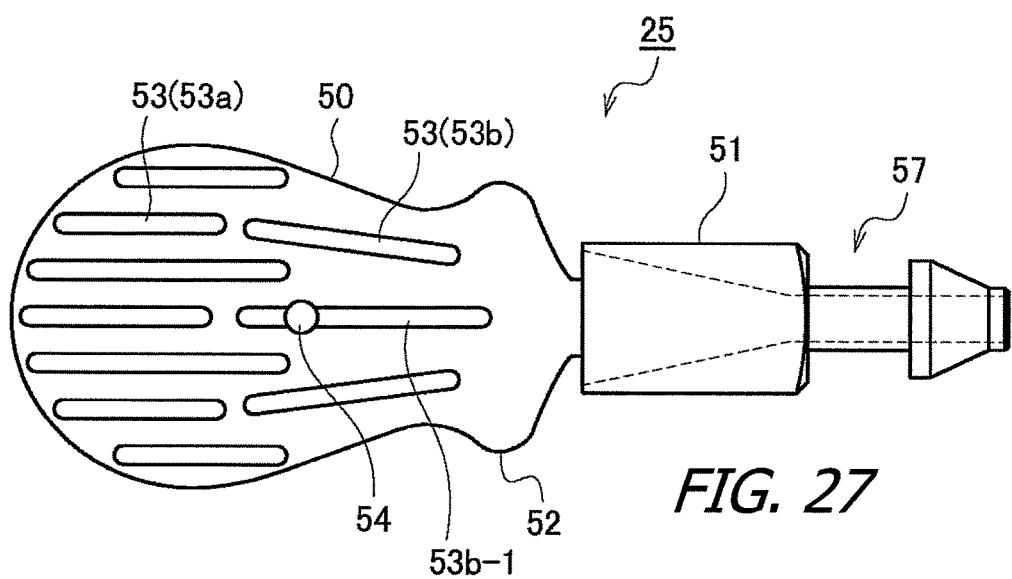
FIG. 27 is a planar view illustrating the configuration of the support member included in the therapeutic instrument according to a fourth embodiment of the present invention.

A fourth embodiment of the present invention is a combination of the first embodiment, the second embodiment, and the third embodiment. Specifically, similarly to the third embodiment, the first through hole 31 is formed on the cylindrical portion 30 of the nozzle member 23 (see FIG. 22 and FIG. 23), and as illustrated in FIG. 27, the second through hole 54 is formed by adding a plurality of protrusions 53 on the surface of the supporting portion 50 of the support member 25, so as to correspond to the first through hold 31. The second through hole 54 is formed in a longitudinally middle part of the rear end side protrusion 53b-1. The protruding dimension of the rear end side protrusion 53b may be set to be larger than the tip side protrusion 53a, or all of the rear end side protrusions 53b may be set in the same protruding dimension.

In the therapeutic instrument 20 having the abovementioned configuration, the following effect can be obtained, in addition to the effect similar to the first to third embodiments. That is, the corneal endothelium layer 2e can be more smoothly pushed-out to outside of the cylindrical portion 30 by injecting the medical water into the cylindrical portion 30 through the first through hole 31 of the nozzle member 23 and the second through hole 54 of the supporting portion 50, and separating the corneal endothelium layer 2e from the supporting portion 50 utilizing the water flow formed by the injected medical water.

9. Explanation for a Fifth Embodiment

The therapeutic instrument according to a fifth embodiment of the present invention is characterized particularly in the configurations of the nozzle member 23 and the support member 25. Explanation will be given hereafter.

Figure 28:
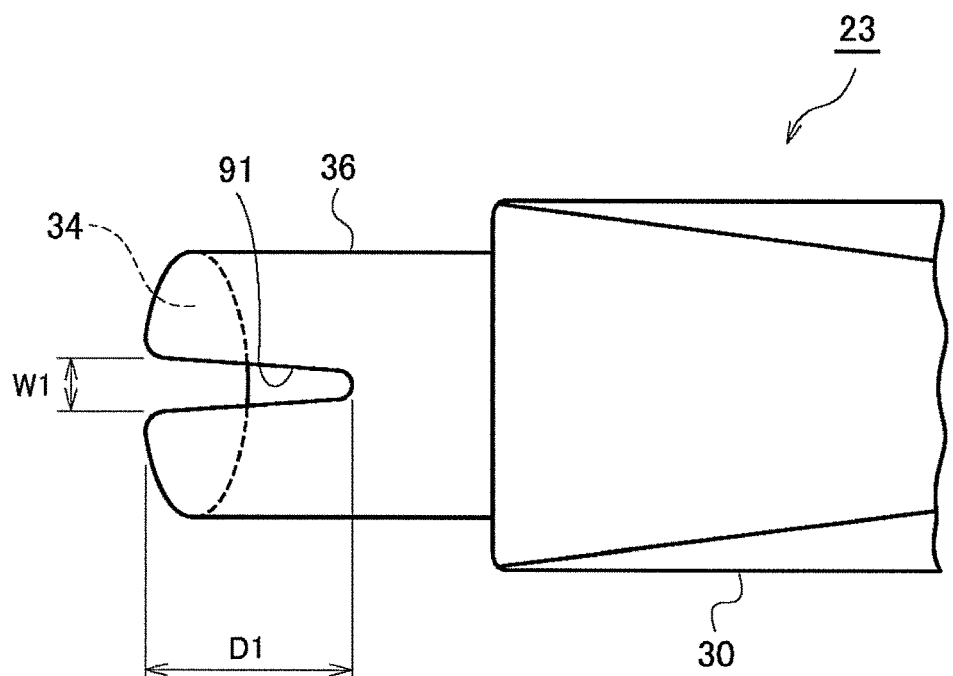
FIG. 28 is a planar view of an essential part illustrating the configuration of the nozzle member included in the therapeutic instrument according to a fifth embodiment of the present invention.
Figure 29:
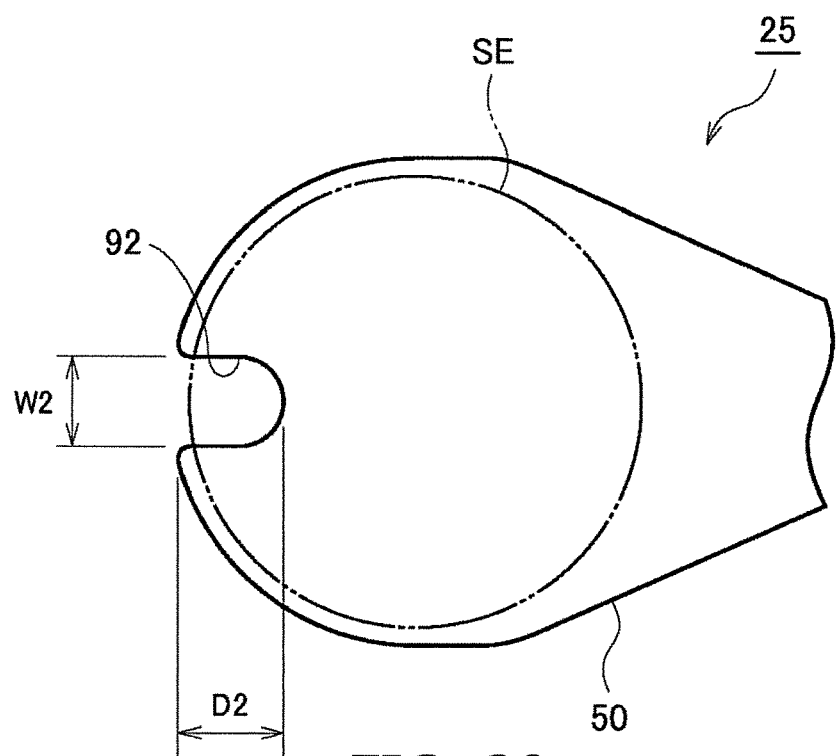
FIG. 29 is a planar view of an essential part illustrating the configuration of the support member included in the therapeutic instrument according to a fifth embodiment of the present invention.

FIG. 28 is a planar view of an essential part illustrating the configuration of the nozzle member included in the therapeutic instrument according to a fifth embodiment of the present invention, and FIG. 29 is a planar view of an essential part illustrating the configuration of the support member included in the therapeutic instrument according to a fifth embodiment of the present invention.

In this embodiment, a first notch 91 is formed on the tip of the cylindrical portion 30 of the nozzle member 23, and a second notch 92 is formed on the tip of the supporting portion 50 of the support member 25 corresponding to the first notch 91.

The first notch 91 is formed into approximately V-shape in such a manner as cutting into the beak portion 36 of the cylindrical portion 30 from a tip edge thereof in an axial direction (right and left direction in the figure) of the nozzle member 23. Further, the first notch 91 is formed in such a manner as cutting into the beak portion 36 from an edge of the side largely protruding frontward, on a peripheral edge of the opening 34 which is obliquely cut on the tip of the beak portion 36. A depth dimension D1 of the first notch 91 is set to be larger than a depth dimension D2 of the second notch 92. A width dimension W1 of the first notch 91 is set to be smaller than a width dimension W2 of the second notch 92. Further, the width dimension W1 of the first notch 91 becomes largest at a tip edge portion of the beak portion 36, and becomes gradually narrower as it goes away from this portion.

Figure 30A:
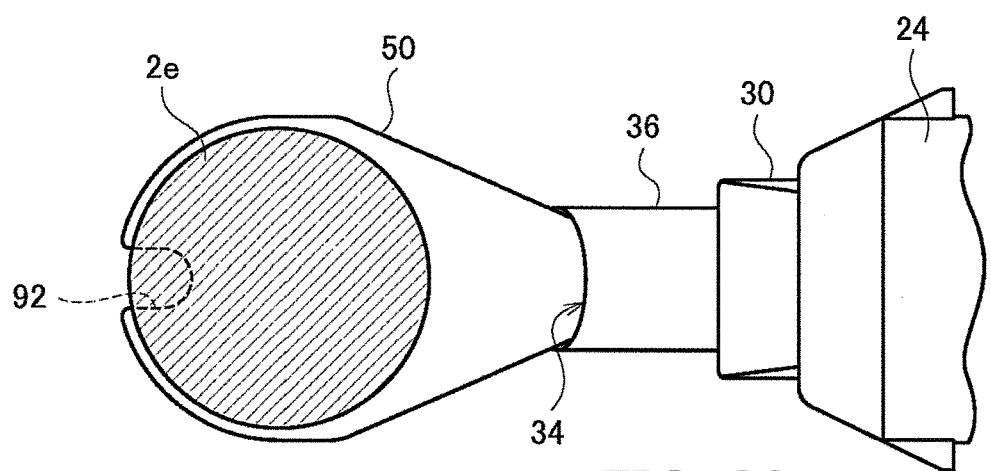
FIGS. 30A and 30B are plan and lower side views illustrating a state of placing a corneal endothelial layer on the supporting portion.
Figure 30B:
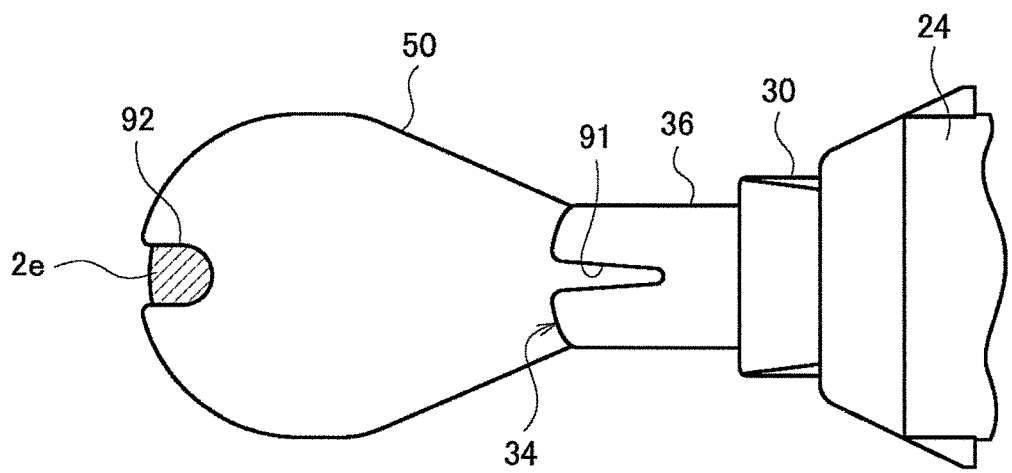

The second notch 92 is formed into approximately U-shape on the supporting portion 50, in such a manner as cutting into the supporting portion 50 from a tip edge thereof in an axial direction of the support member 25. Further, the second notch 92 is formed in such a manner as cutting into the supporting portion 50 so as to reach the support region SE in which the corneal endothelium layer 2e is supported. Therefore, when the corneal endothelium layer 2e is placed on the supporting portion 50, as illustrated in a planar view of FIG. 30A, and a lower side view of FIG. 30B, a part of the corneal endothelium layer 2e supported by the supporting portion 50 is set in an overlapping (covering) state on the second notch 92.

Figure 31A:
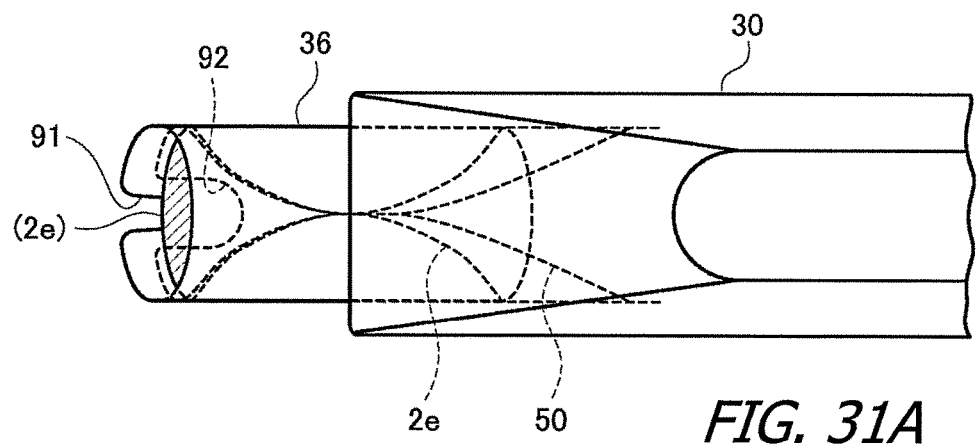
FIGS. 31A and 31B are plan and lower side views illustrating a state of housing the supporting portion supporting the corneal endothelial layer in the cylindrical portion.
Figure 31B:
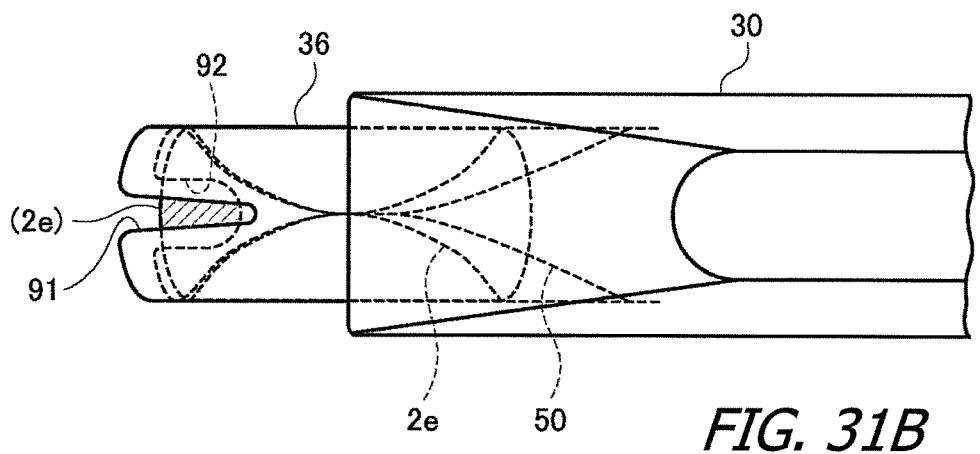
Figure 32:
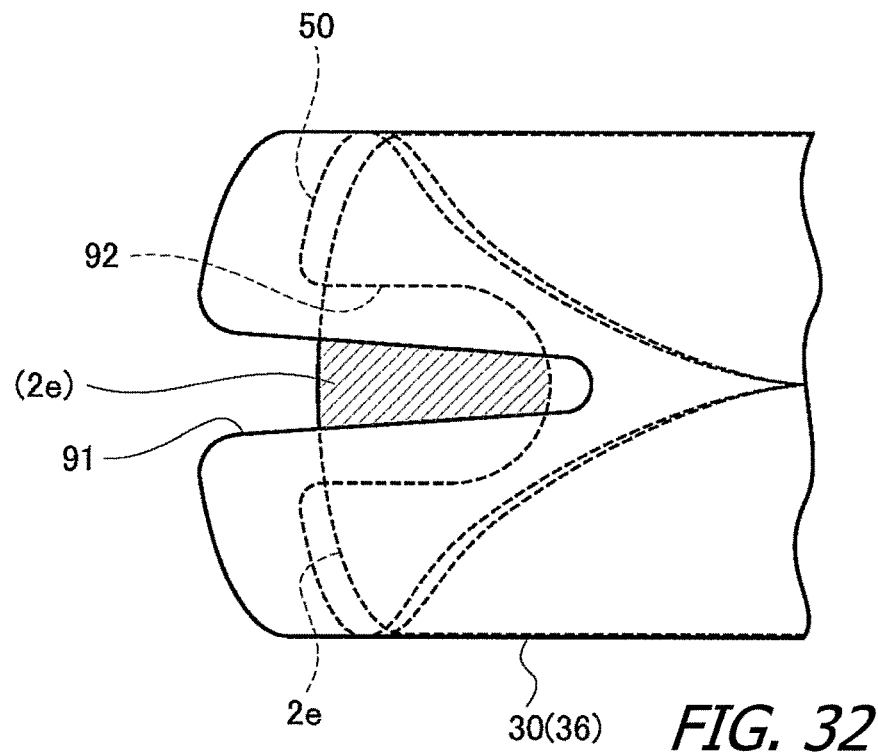
FIG. 32 is an expanded view of a part of FIG. 31B.

When the therapeutic instrument 20 according to the fifth embodiment of the present invention is used, the nozzle member 23 is most advanced so as to suck the corneal endothelium layer 2e supported by the supporting portion 50 into the cylindrical portion 30 by the negative pressure, in the storage process described in the first embodiment. Then, as illustrated in a planar view of FIG. 31A, and a lower side view of FIG. 31B, the first notch 91 and the second notch 92 are set in an overlapped state on each other. Further, the supporting portion 50 is stored in the cylindrical portion 30 in a state of being deformed into a roll-shape, together with the corneal endothelium layer 2e. In this state, as illustrated in FIG. 32, a part of the corneal endothelium layer 2e is exposed to outside, at a place where the first notch 91 formed on the tip of the cylindrical portion 30 and the second notch 92 formed on the tip of the supporting portion 50 are overlapped on each other. Therefore, a part of the corneal endothelium layer 2e can be directly confirmed visually from outside, even in a state in which the supporting portion 50 is housed in the cylindrical portion 30.

Figure 33:
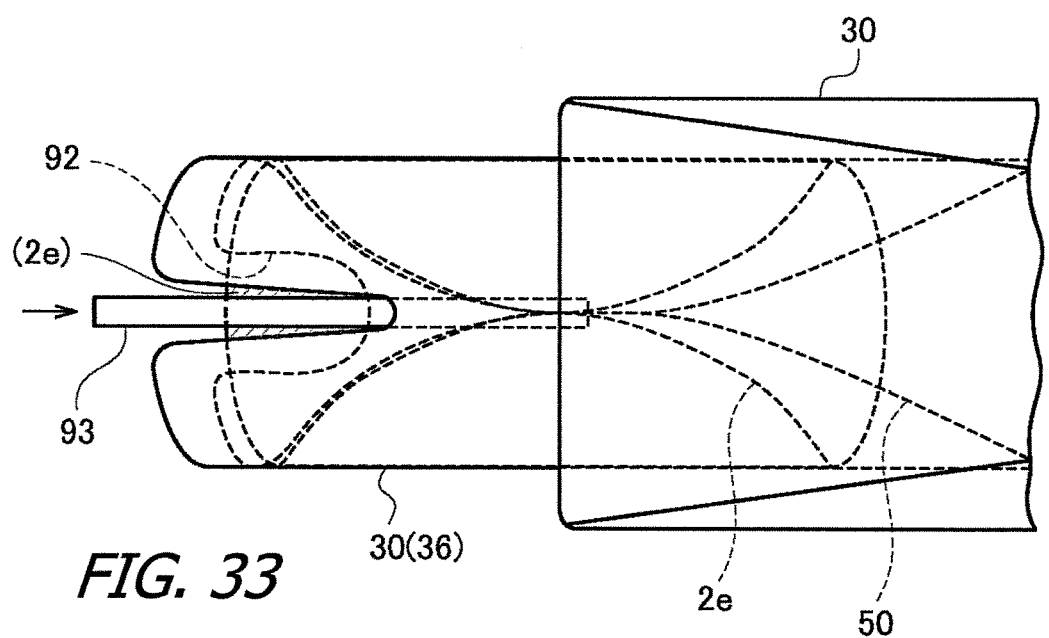
FIG. 33 is a view illustrating a method of injecting a medical water of the firth embodiment.

In the pushing process thereafter, the medical water is injected into the cylindrical portion 30 as needed, from the place where the first notch 91 and the second notch 92 are overlapped on each other, before the therapeutic instrument 20 is approached to the eyeball. For example as illustrated in FIG. 33, injection of the medical water is performed by inserting a thin feeding tube 93 such as an injection needle, etc., into the cylindrical portion 30, from the place where the first notch 91 and the second notch 92 are overlapped on each other. At this time, the feeding tube 93 is inserted into the place where the corneal endothelium layer 2e and the supporting portion 50 are faced each other, and the medical water is injected into the cylindrical portion 30 through the feeding tube 93. Thus, the medical water flows to the place where the supporting portion 50 and the corneal endothelium layer 2e are faced each other, to thereby form the water flow there. Accordingly, even if the supporting portion 50 and the corneal endothelium layer 2e are stuck to each other, the supporting portion 50 and the corneal endothelium layer 2e are set in a separated state (peeled-off state) due to such a formation of the water flow. Accordingly, when pushing operation of the plunger 75 is performed, the corneal endothelium layer 2e can be surely separated from the supporting portion 50, and can be pushed-out to outside the cylindrical portion 30.

Further, in the fifth embodiment of the present invention, as described above, a part of the corneal endothelium layer 2e is disposed so as to be exposed to outside, even if the supporting portion 50 is stored in the cylindrical portion 30. Therefore, this embodiment can respond to not only a system of pushing-out the corneal endothelium layer 2e to outside by performing pushing operation of the plunger 75, but also a system of gripping the corneal endothelium layer 2e in the cylindrical portion 30 and pulling-out it to outside the cylindrical portion 30. Specifically, for example, a forceps is inserted into an eye from elsewhere from an incision, in a state of inserting the beak portion 36 of the cylindrical portion 30 into the incision of a cornea portion. Next, a tip part (grip part) of the forceps is advanced to the place where the first notch 91 and the second notch 92 are overlapped on each other, to thereby grip the corneal endothelium layer 2e by the forceps, the corneal endothelium layer 2e being exposed there. Next, by moving the forceps while gripping the corneal endothelium layer 2e, the corneal endothelium layer 2e is pulled-out to outside the cylindrical portion 30. At this time, the corneal endothelium layer 2e can be smoothly pulled-out from the cylindrical portion 30 by separating the corneal endothelium layer 2e from the supporting portion 50 by injecting the medical water as described above. Therefore, a risk of damaging the corneal endothelial layer 2e becomes small.

When the abovementioned drawing system is employed, the positive pressure generator is not required, for pushing-out the therapeutic agent to outside the cylindrical portion. An aspect of the present invention in this case, will be supplementarily described hereafter.

Supplementary Description

There is provided a therapeutic instrument, including:

a support member having a tongue-shaped supporting portion for supporting a sheet-like therapeutic agent;

a nozzle member having a cylindrical portion in which the supporting portion supporting the therapeutic agent can be housed, and having an opening on a tip of the cylindrical portion, through which the supporting portion can be loaded and unloaded in/from the cylindrical portion; and a water flow forming part that forms a water flow at a place where the supporting portion and the therapeutic agent are faced each other, when a medical water is fed into the cylindrical portion in a state in which the therapeutic agent is housed in the cylindrical portion together with the supporting portion, the water flow forming part including:

a first notch formed on a tip of the cylindrical portion; and
a second notch formed on a tip of the supporting portion so as to correspond to the first notch, and overlapped on the first notch in a state in which the supporting portion is housed in the cylindrical portion, wherein the water flow is formed on the place where the supporting portion and the therapeutic agent are faced each other, when a medical water is injected into the cylindrical portion from the place where the first notch and the second notch are overlapped on each other in a state in which the supporting portion supporting the therapeutic agent is housed in the cylindrical portion.

10. Modified Example, Etc

A technical range of the present invention is not limited to the abovementioned embodiments, and includes various modifications and improvements in a range capable of deriving a specific effect obtained by constituting features of the invention and a combination of them.

For example, in the first embodiment (FIG. 8), as a preferable aspect, protrusions 53 are formed at both sides of the tip side and the rear side of the supporting portion 50. However, the present invention is not limited thereto, and may include a case in which one or a plurality of protrusions 53 are formed only on the rear end side of the supporting portion 50.

Further, in each of the abovementioned embodiments, the base portion 51 is formed integrally with the support member 25 having the supporting portion 50. However, the present invention is not limited thereto, and the support member 25 and the base portion 51 may be constituted as separate members.

Further, the pressing member 29 for preventing prolapse of iris is not a necessary member for the corneal endothelial transplant surgery, and therefore may be provided as needed.

Further, regarding the shape and the dimension of each protrusion 53 when a plurality of protrusions 53 is formed on the supporting portion 50 of the support member 25, various modifications are acceptable.

Further, in the third embodiment, the positive pressure generator is constituted using the syringe unit 22. However, the present invention is not limited thereto, and for example, the positive pressure generator may be constituted by a combination of a tube and a pump.

Further, the present invention may be executed by suitably combining abovementioned each embodiment. Specifically, the present invention may be executed in a combination of the first embodiment and the fifth embodiment, in a combination of the second embodiment and the fifth embodiment, in a combination of the third embodiment and the fifth embodiment, and in a combination of the fourth embodiment and the fifth embodiment.

DESCRIPTION OF SIGNS AND NUMERALS

20 Therapeutic instrument
21 Body unit
22 Syringe unit
23 Nozzle member
24 Holding member
25 Support member
26 Sealing member
27 Needle member
28 Connecting member
29 Pressing member
31 First through hole
34 Opening
50 Supporting portion
53 Protrusion 54 Second through hole
91 First notch
92 Second notch

The invention claimed is:

1. A therapeutic instrument, comprising:
a support member having a tongue-shaped supporting portion for supporting a sheet-like therapeutic agent;
a nozzle member having a cylindrical portion in which the supporting portion supporting the therapeutic agent can be housed, and having an opening on a tip of the cylindrical portion, through which the supporting portion can be loaded and unloaded in/from the cylindrical portion;
a positive pressure generator that adds a positive pressure in the cylindrical portion for pushing-out the therapeutic agent housed in the cylindrical portion together with the supporting portion, to outside the cylindrical portion through the opening; and
a water flow forming part that forms a water flow, at a place where the supporting portion and the therapeutic agent are facing each other, when a medical water is fed into the cylindrical portion in a state in which the therapeutic agent is housed in the cylindrical portion together with the supporting portion, wherein
the positive pressure generator is configured to generate a positive pressure in the cylindrical portion by feeding the medical water into the cylindrical portion from a rear end side of the cylindrical portion, and
the water flow forming part includes one or a plurality of protrusions formed on a surface of the supporting portion for supporting the therapeutic agent by floating the therapeutic agent from the surface of the supporting portion, and configured to form the water flow by introducing the medical water fed by the positive pressure generator to a place between the supporting portion and the therapeutic agent where the supporting portion and the therapeutic agent are facing each other.

2. The therapeutic instrument according to claim 1, wherein in the plurality of protrusions, a protruding dimension of a protrusion positioned on an upstream side of the water flow formed by the water flow forming part, is set to be larger than a protruding dimension of a protrusion positioned on a downstream side thereof of the water flow formed by the water flow forming part.

3. The therapeutic instrument according to claim 2, wherein the water flow forming part includes a first through hole formed on the cylindrical portion, and a second through hole formed on the supporting portion so as to correspond to the first through hole, and overlapped on the first through hole in the state in which the supporting portion is housed in the cylindrical portion, and is configured to form the water flow at the place where the supporting portion and the therapeutic agent are facing each other, when the medical water is injected into the cylindrical portion through the first through hole and the second through hole in the state in which the supporting portion supporting the therapeutic agent is housed in the cylindrical portion.

4. The therapeutic instrument according to claim 2, wherein the water flow forming part includes a first notch formed on a tip of the cylindrical portion, and a second notch formed on a tip of the supporting portion so as to correspond to the first notch, and overlapped on the first notch in the state in which the supporting portion is housed in the cylindrical portion, and is configured to form the water flow at a portion where the supporting portion and the therapeutic agent are facing each other, when the medical water is fed into the cylindrical portion from a place where the first notch and the second notch are overlapped on each other in the state in which the supporting portion supporting the therapeutic agent is housed in the cylindrical portion.

5. The therapeutic instrument according to claim 1, wherein the water flow forming part includes a first through hole formed on the cylindrical portion, and a second through hole formed on the supporting portion so as to correspond to the first through hole, and overlapped on the first through hole in the state in which the supporting portion is housed in the cylindrical portion, and is configured to form the water flow at the place where the supporting portion and the therapeutic agent are facing each other, when the medical water is injected into the cylindrical portion through the first through hole and the second through hole in the state in which the supporting portion supporting the therapeutic agent is housed in the cylindrical portion.

6. The therapeutic instrument according to claim 1, wherein the water flow forming part includes a first notch formed on a tip of the cylindrical portion, and a second notch formed on a tip of the supporting portion so as to correspond to the first notch, and overlapped on the first notch in the state in which the supporting portion is housed in the cylindrical portion, and is configured to form the water flow at a portion where the supporting portion and the therapeutic agent are facing each other, when the medical water is fed into the cylindrical portion from a place where the first notch and the second notch are overlapped on each other in the state in which the supporting portion supporting the therapeutic agent is housed in the cylindrical portion.

7. A therapeutic instrument, comprising:
a support member having a tongue-shaped supporting portion for supporting a sheet-like therapeutic agent;
a nozzle member having a cylindrical portion in which the supporting portion supporting the therapeutic agent can be housed, and having an opening on a tip of the cylindrical portion, through which the supporting portion can be loaded and unloaded in/from the cylindrical portion;
a positive pressure generator that adds a positive pressure in the cylindrical portion for pushing-out the therapeutic agent housed in the cylindrical portion together with the supporting portion, to outside the cylindrical portion through the opening; and
a water flow forming part that forms a water flow, at a place where the supporting portion and the therapeutic agent are facing each other, when a medical water is fed into the cylindrical portion in a state in which the therapeutic agent is housed in the cylindrical portion together with the supporting portion, wherein
the water flow forming part includes a first through hole formed on the cylindrical portion, and a second through hole that extends through the supporting portion so as to correspond to the first through hole, and overlapped on the first through hole in the state in which the supporting portion is housed in the cylindrical portion, and is configured to form the water flow between the supporting portion and the therapeutic agent at the place where the supporting portion and the therapeutic agent are facing each other, when the medical water is injected into the cylindrical portion through the first through hole and the second through hole in the state in which the supporting portion supporting the therapeutic agent is housed in the cylindrical portion.

8. A therapeutic instrument, comprising:
a support member having a tongue-shaped supporting portion for supporting a sheet-like therapeutic agent;

a nozzle member having a cylindrical portion in which the supporting portion supporting the therapeutic agent can be housed, and having an opening on a tip of the cylindrical portion, through which the supporting portion can be loaded and unloaded in/from the cylindrical portion;

a positive pressure generator that adds a positive pressure in the cylindrical portion for pushing-out the therapeutic agent housed in the cylindrical portion together with the supporting portion, to outside the cylindrical portion through the opening; and a water flow forming part that forms a water flow, at a place where the supporting portion and the therapeutic agent are facing each other, when a medical water is fed into the cylindrical portion in a state in which the therapeutic agent is housed in the cylindrical portion together with the supporting portion, wherein the water flow forming part includes a first notch formed on a tip of the cylindrical portion, and a second notch formed on a tip of the supporting portion so as to correspond to the first notch, and overlapped on the first notch in the state in which the supporting portion is housed in the cylindrical portion, and is configured to form the water flow between the supporting portion and the therapeutic agent at a portion where the supporting portion and the therapeutic agent are facing each other, when the medical water is fed into the cylindrical portion from a place where the first notch and the second notch are overlapped on each other in the state in which the supporting portion supporting the therapeutic agent is housed in the cylindrical portion.

* * * * *